US012669911B2

(12) United States Patent
Imura et al.

(10) Patent No.: US 12,669,911 B2
(45) Date of Patent: Jun. 30, 2026

(54) GRAPHICAL USER INTERFACE FOR INTRAVASCULAR ULTRASOUND AUTOMATED LESION ASSESSMENT SYSTEM

(71) Applicant: BOSTON SCIENTIFIC SCIMED, INC., Maple Grove, MN (US)

(72) Inventors: Haruka Imura, Maple Grove, MN (US); Jennifer Gibbs, White Bear, MN (US); Erik Stephen Freed, New Brighton, MN (US); Judith Tiferes Wang, Buenos Aires (AR); Luke Brossman, Minneapolis, MN (US); Melanie Loppnow, Minneapolis, MN (US); Wenguang Li, Los Gatos, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 41 days.

(21) Appl. No.: 18/367,883

(22) Filed: Sep. 13, 2023

(65) Prior Publication Data

US 2024/0086025 A1 Mar. 14, 2024

Related U.S. Application Data

(60) Provisional application No. 63/406,353, filed on Sep. 14, 2022.

(51) Int. Cl.
*G06F 3/048* (2013.01)
*A61B 8/00* (2006.01)
(Continued)

(52) U.S. Cl.
CPC ............ *G06F 3/0481* (2013.01); *A61B 8/465* (2013.01); *A61B 8/469* (2013.01);
(Continued)

(58) Field of Classification Search
CPC ... G06F 3/0481; G06F 3/04845; A61B 8/465; A61B 8/469; G06T 11/203
See application file for complete search history.

(56) References Cited

U.S. PATENT DOCUMENTS

| | | | |
|---|---|---|---|
| 6,945,938 B2 | 9/2005 | Grunwald | |
| 7,306,561 B2 | 12/2007 | Sathyanarayana | |

(Continued)

FOREIGN PATENT DOCUMENTS

| | | |
|---|---|---|
| CA | 3133449 A1 | 9/2020 |
| CN | 115052529 A | 9/2022 |

(Continued)

OTHER PUBLICATIONS

International Search Report and Written Opinion dated Dec. 11, 2023 for International Application No. PCT/US2023/032643.

*Primary Examiner* — David Phantana-angkool
(74) *Attorney, Agent, or Firm* — Seager Tufte & Wickhem, LLP

(57) ABSTRACT

The present disclosure provides a graphical user interface (GUI) arranged to convey information related to the IVUS images and lesion assessment and provide for the user to manipulate the information. The GUIs can be generated to include a cross-section view without assessments post recording of IVUS images and to depict assessments after navigation through frames of the IVUS images.

18 Claims, 26 Drawing Sheets

(51) Int. Cl.

| | |
|---|---|
| *G06F 3/0481* | (2022.01) |
| *G06F 3/04845* | (2022.01) |
| *G06T 11/20* | (2006.01) |
| *A61B 8/12* | (2006.01) |

(52) U.S. Cl.

CPC ........ *G06F 3/04845* (2013.01); *G06T 11/203* (2013.01); *A61B 8/12* (2013.01); *G06T 2200/24* (2013.01); *G06T 2210/41* (2013.01)

(56) References Cited

U.S. PATENT DOCUMENTS

| | | | |
|---|---|---|---|
| 7,426,959 | B2 | 9/2008 | Wang et al. |
| 10,542,954 | B2 * | 1/2020 | Spencer ................. A61B 6/487 |
| 11,742,070 | B2 * | 8/2023 | Grady ................ G06F 16/5866 |
| | | | 382/278 |
| 12,167,896 | B2 * | 12/2024 | Zheng ................... A61B 8/488 |
| 12,201,477 | B2 * | 1/2025 | Kemp ...................... A61B 8/12 |
| 12,262,872 | B2 * | 4/2025 | Petersen ............. A61B 1/0017 |
| 12,364,385 | B2 * | 7/2025 | Douk ................. A61B 1/00172 |
| 12,527,478 | B2 * | 1/2026 | Massimini ......... A61B 5/02007 |
| 2006/0100522 | A1 | 5/2006 | Yuan et al. |
| 2006/0106320 | A1 | 5/2006 | Barbato |
| 2006/0173350 | A1 | 8/2006 | Yuan et al. |
| 2006/0253028 | A1 | 11/2006 | Lam et al. |
| 2007/0016054 | A1 | 1/2007 | Cao et al. |
| 2007/0038111 | A1 | 2/2007 | Rehrig et al. |
| 2010/0331695 | A1 * | 12/2010 | Nair ................... A61B 5/02007 |
| | | | 600/443 |
| 2012/0283569 | A1 * | 11/2012 | Ciompi ................ A61B 8/4461 |
| | | | 600/463 |
| 2015/0182192 | A1 | 7/2015 | Kaneko |
| 2015/0257850 | A1 * | 9/2015 | Sakamoto .............. G16H 50/30 |
| | | | 600/407 |
| 2016/0335766 | A1 * | 11/2016 | Ambwani ................. G06T 7/11 |
| 2017/0332999 | A1 | 11/2017 | Coolidge et al. |
| 2019/0099080 | A1 | 4/2019 | Kunio et al. |
| 2019/0282199 | A1 * | 9/2019 | Merritt ................... A61B 8/085 |
| 2019/0365480 | A1 * | 12/2019 | Gopinath ............. A61B 5/4851 |
| 2020/0029861 | A1 * | 1/2020 | Rajguru ................. A61B 8/12 |
| 2020/0121291 | A1 * | 4/2020 | Cai ...................... A61B 8/5207 |
| 2021/0128099 | A1 * | 5/2021 | Al-Noor ............. G06N 3/0895 |
| 2023/0135562 | A1 * | 5/2023 | Misener .............. A61B 8/4254 |
| | | | 600/454 |
| 2023/0138970 | A1 * | 5/2023 | Sowards .............. A61B 8/0841 |
| | | | 600/437 |
| 2024/0331152 | A1 * | 10/2024 | Wang ................... A61B 8/5223 |
| 2024/0382181 | A1 * | 11/2024 | Shang ................... A61B 8/464 |
| 2025/0255577 | A1 * | 8/2025 | Bedi ...................... A61B 8/06 |

FOREIGN PATENT DOCUMENTS

| | | | |
|---|---|---|---|
| WO | 2014073016 | A1 | 5/2014 |
| WO | 2014092755 | A1 | 6/2014 |
| WO | 2020084039 | A1 | 4/2020 |
| WO | 2024059141 | A1 | 3/2024 |

* cited by examiner

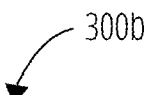
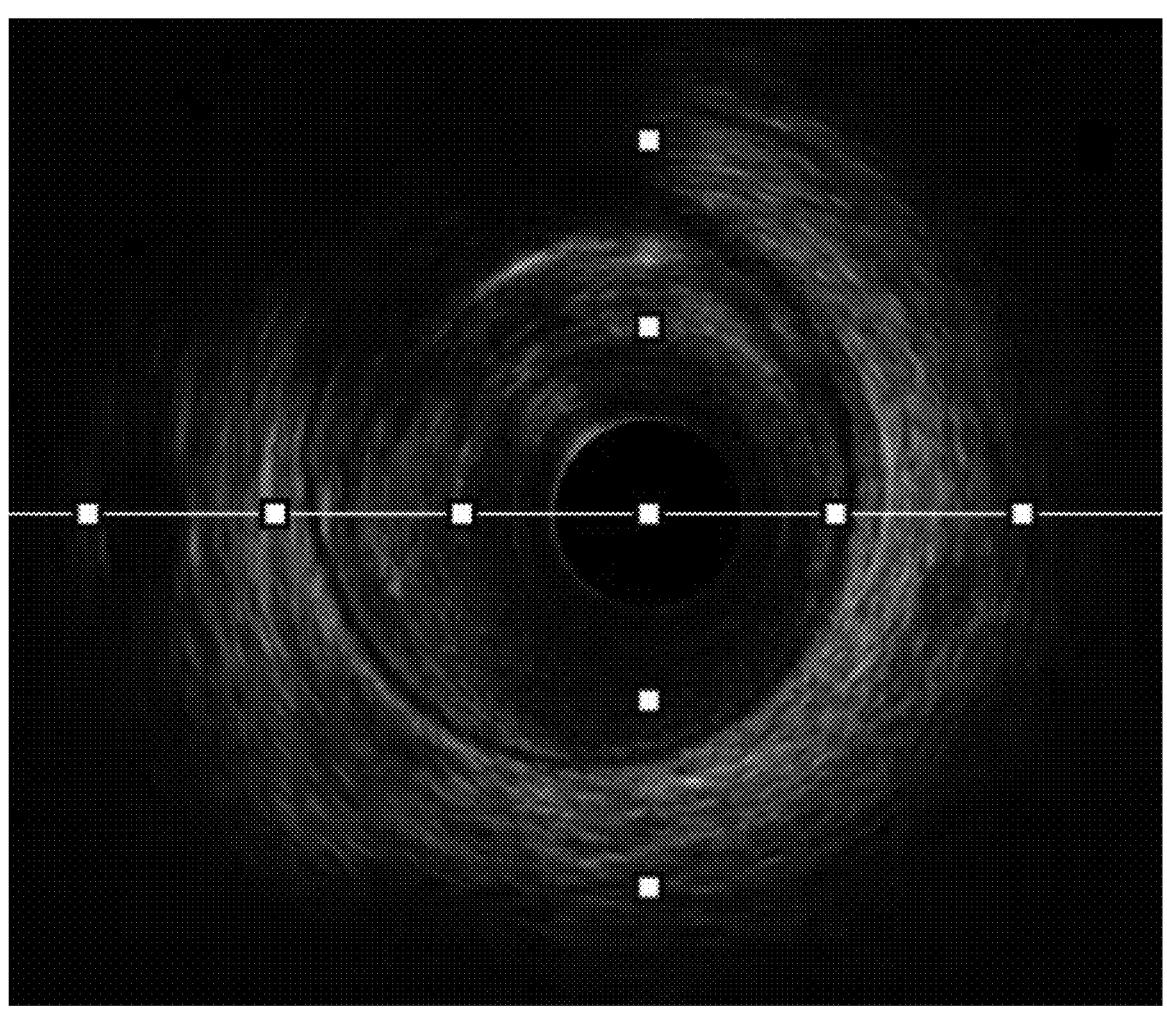
FIG. 3B

INTERACTIVE CROSS SECTIONAL DUAL VIEW

1700

RECEIVE A SERIES OF INTRAVASCULAR ULTRASOUND (IVUS) IMAGES OF A VESSEL OF A PATIENT, THE SERIES OF IVUS IMAGES COMPRISING A PLURALITY OF FRAMES 1702

GENERATE A FIRST GRAPHICAL USER INTERFACE (GUI) COMPONENT COMPRISING AN INDICATION OF A CROSS-SECTION VIEW OF A ONE OF THE PLURALITY OF FRAMES 1704

GENERATE A SECOND GUI COMPONENT COMPRISING INDICATIONS OF AT LEAST ONE MENU OPTION 1706

GENERATE A THIRD GUI COMPONENT COMPRISING INDICATIONS OF AT LEAST ONE LAYOUT OPTION 1708

GENERATE A FOURTH GUI COMPONENT COMPRISING INDICATIONS OF NAVIGATION INPUTS 1710

GENERATE A GUI COMPRISING THE FIRST, SECOND, THIRD, AND FOURTH GUI COMPONENTS, WHEREIN THE FIRST GUI COMPONENT IS DISPOSED BETWEEN THE SECOND AND THIRD GUI COMPONENTS 1712

RENDER THE GUI FOR DISPLAY ON A DISPLAY 1714

FIG. 17

GRAPHICAL USER INTERFACE FOR INTRAVASCULAR ULTRASOUND AUTOMATED LESION ASSESSMENT SYSTEM

CROSS-REFERENCE TO RELATED APPLICATIONS

This application claims the benefit of U.S. Provisional Patent Application Ser. No. 63/406,353 filed on Sep. 14, 2022, the disclosure of which is incorporated herein by reference.

TECHNICAL FIELD

The present disclosure generally relates to intravascular ultrasound (IVUS) imaging systems. Particularly, but not exclusively, the present disclosure relates to an improved graphical user interface for IVUS imaging systems.

BACKGROUND

Ultrasound devices insertable into patients have proven diagnostic capabilities for a variety of diseases and disorders. For example, intravascular ultrasound (IVUS) imaging systems have been used as an imaging modality for diagnosing blocked blood vessels and providing information to aid medical practitioners in selecting and placing stents and other devices to restore or increase blood flow.

IVUS imaging systems includes a control module (with a pulse generator, an image acquisition and processing components, and a monitor), a catheter, and a transducer disposed in the catheter. The transducer-containing catheter is positioned in a lumen or cavity within, or in proximity to, a region to be imaged, such as a blood vessel wall or patient tissue in proximity to a blood vessel wall. The pulse generator in the control module generates electrical pulses that are delivered to the transducer and transformed to acoustic pulses that are transmitted through patient tissue. The patient tissue (or other structure) reflects the acoustic pulses and reflected pulses are absorbed by the transducer and transformed to electric pulses. The transformed electric pulses are delivered to the image acquisition and processing components and converted into images displayable on the monitor.

However, it can be difficult for physicians to visualize the complete structure of the patient lumen (e.g., vessel) from the raw IVUS images. For example, it is difficult to determine an overall plaque burden, the appropriate size of stent (e.g., diameter and/or length) to use in correcting any strictures in the lumen, as well as the location to land the stent. Thus, there here is a need for user interfaces, and particularly graphical user interfaces, that communicate information from the IVUS system to a user.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In general, the present disclosure provides to an improvement to computing devices and particularly to IVUS guidance systems in that the present disclosure provides a graphical user interface arranged to convey the wealth of information with which modern IVUS systems generate. For example, an IVUS system may include machine learning features to process and analyze the signals generated during an IVUS run. Such information can include automatic detection of a lesion, key frames related to a lesion, a stent, or the like. The improved graphical user interface provided herein includes displaying such information as well as providing a method for a user to manipulate the information as needed.

In some implementations, the present disclosure be embodied as a method, for example, a method for an intravascular ultrasound (IVUS) imaging system, comprising: receiving a series of intravascular ultrasound (IVUS) images of a vessel of a patient, the series of IVUS images comprising a plurality of frames; generating a first graphical user interface (GUI) component comprising an indication of a cross-section view of a one of the plurality of frames; generating a second GUI component comprising indications of at least one menu option; generating a third GUI component comprising indications of at least one layout option; generating a fourth GUI component comprising indications of navigation inputs, the navigation inputs comprising an assessment button; generating a GUI comprising the first, second, third, and fourth GUI components, wherein the first GUI component is disposed between the second and third GUI components; and rendering the GUI for display on a display.

Alternatively, or additionally any of the embodiments of a method above can comprise generating the fourth GUI component comprising indications of the assessment button and a distal bracket and a proximal bracket, wherein the distal bracket and the proximal bracket are moveable.

Alternatively, or additionally any of the embodiments of a method above can comprise receiving an indication, via an input device, to move the distal bracket, the proximal bracket, or the distal bracket and the proximal bracket.

Alternatively, or additionally any of the embodiments of a method above can comprise regenerating the fourth GUI component comprising graphical indications of the moved distal bracket, the moved proximal bracket, or the moved distal and proximal bracket and the assessment button.

Alternatively, or additionally any of the embodiments of a method above can comprise wherein the assessment button is disposed between the proximal bracket and the distal bracket.

Alternatively, or additionally any of the embodiments of a method above can comprise determining a distance between the distal bracket and the proximal bracket; and generating the indication of the assessment button based on the distance.

Alternatively, or additionally any of the embodiments of a method above can comprise determining whether the distance is greater than a threshold; and generating the indication of the assessment button comprising a graphical representation including at least an icon and text based on a determination that the distance is greater than the threshold.

Alternatively, or additionally any of the embodiments of a method above can comprise generating the indication of the assessment button comprising a graphical representation including one but not both of text or an icon based on a determination that the distance is less than or equal to the threshold.

Alternatively, or additionally any of the embodiments of a method above can comprise receiving an indication, via an input device, the assessment button was clicked; and generating a fifth GUI component comprising an indication of the distal bracket, the proximal bracket, a minimum region, a vessel profile view and a mirror of the vessel profile view.

Alternatively, or additionally any of the embodiments of a method above can comprise, wherein the vessel profile view comprises an indication of a border of the vessel and a border of a lumen within the vessel represented along a longitudinal axis of the vessel.

Alternatively, or additionally any of the embodiments of a method above can comprise receiving an indication of the vessel border and the lumen border for each of the plurality of frames; generating a graphical representation of the border of the vessel and the border of the lumen based on the indication; generating the profile view comprising the graphical representation of the border of the vessel and the border of the lumen; and mirroring the vessel profile view about a central longitudinal axis to generate the mirror of the vessel profile view.

Alternatively, or additionally any of the embodiments of a method above can comprise: receiving, from a machine learning automated border detection model, the indication of the vessel border and the lumen border; receiving an indication of a confidence of the vessel border for each of the plurality of frames; determining, for each of the plurality of frames, whether the confidence is less than or equal to a threshold confidence level; and generating the graphical representation of the vessel border for a first portion of the central longitudinal axis comprising a first graphical representation based on a determination that the confidence is less than or equal to the threshold for the plurality of frames associated with the first portion; and generating the graphical representation of the vessel border for a second portion of the central longitudinal axis comprising a second graphical representation based on a determination that the confidence is not less than or equal to the threshold for the plurality of frames associated with the second portion, wherein the second graphical representation is different than the first graphical representation.

Alternatively, or additionally any of the embodiments of a method above can comprise, wherein the first graphical representation comprises a first color, first width, or first style of line and wherein the second graphical representation comprises a second color, second width, or second style of line.

In some implementations, the present disclosure be embodied as an apparatus, comprising a processor coupled to a memory, the memory comprising instructions executable by the processor, the processor configured to couple to an intravascular ultrasound (IVUS) imaging system and configured to execute the instructions, which instructions when executed cause the processor to implement the method of any combination of the examples above.

In some implementations, the present disclosure be embodied as at least one machine readable storage device, comprising a plurality of instructions that in response to being executed by a processor of an intravascular ultrasound (IVUS) imaging system cause the processor to implement the method of any combination of the examples above.

In some implementations, the present disclosure be embodied as an apparatus for an intravascular ultrasound (IVUS) imaging system, comprising: a display; an interface configured to couple to an IVUS catheter; a processor coupled to the interface and the display; and a memory device comprising instructions, which when executed by the processor cause the IVUS imaging system to: receive a series of intravascular ultrasound (IVUS) images of a vessel of a patient, the series of IVUS images comprising a plurality of frames; generate a first graphical user interface (GUI) component comprising an indication of a cross-section view of a one of the plurality of frames; generate a second GUI component comprising indications of at least one menu option; generate a third GUI component comprising indications of at least one layout option; generate a fourth GUI component comprising indications of navigation inputs, the navigation inputs comprising an assessment button; generate a GUI comprising the first, second, third, and fourth GUI components, wherein the first GUI component is disposed between the second and third GUI components; and render the GUI and send the rendered graphical information to the display.

Alternatively, or additionally in any of the embodiments of an apparatus above, the fourth GUI component can comprise indications of the assessment button and a distal bracket and a proximal bracket, and wherein the distal bracket and the proximal bracket are moveable.

Alternatively, or additionally in any of the embodiments of an apparatus above, the memory device can further comprise instructions that when executed by the processor cause the IVUS imaging system to receive, via an input device, an indication to move the distal bracket, the proximal bracket, or the distal bracket and the proximal bracket.

Alternatively, or additionally in any of the embodiments of an apparatus above, the memory device can further comprise instructions that when executed by the processor cause the IVUS imaging system to regenerate the fourth GUI component comprising graphical indications of the moved distal bracket, the moved proximal bracket, or the moved distal and proximal bracket and the assessment button.

Alternatively, or additionally in any of the embodiments of an apparatus above, the assessment button is disposed between the proximal bracket and the distal bracket.

Alternatively, or additionally in any of the embodiments of an apparatus above, the memory device can further comprise instructions that when executed by the processor cause the IVUS imaging system to: determine a distance between the distal bracket and the proximal bracket; and generate the indication of the assessment button based on the distance.

Alternatively, or additionally in any of the embodiments of an apparatus above, the memory device can further comprise instructions that when executed by the processor cause the IVUS imaging system to: determine whether the distance is greater than a threshold; and generate the indication of the assessment button comprising a graphical representation including at least an icon and text based on a determination that the distance is greater than the threshold.

Alternatively, or additionally in any of the embodiments of an apparatus above, the memory device can further comprise instructions that when executed by the processor cause the IVUS imaging system to generate the indication of the assessment button comprising a graphical representation including one but not both of text or an icon based on a determination that the distance is less than or equal to the threshold.

In some implementations, the present disclosure be embodied as at least one machine readable storage device, comprising a plurality of instructions that in response to being executed by a processor of an intravascular ultrasound (IVUS) imaging system cause the processor to: receive a series of intravascular ultrasound (IVUS) images of a vessel of a patient, the series of IVUS images comprising a plurality of frames; generate a first graphical user interface (GUI) component comprising an indication of a cross-section view of a one of the plurality of frames; generate a second GUI component comprising indications of at least one menu option; generate a third GUI component comprising indications of at least one layout option; generate a fourth GUI component comprising indications of navigation inputs, the navigation inputs comprising an assessment button; generate a GUI comprising the first, second, third, and fourth GUI components, wherein the first GUI component is disposed between the second and third GUI components; and render the GUI for display on a display.

Alternatively, or additionally in any of the embodiments of an at least one machine readable storage device above, the instructions in response to being executed by the processor can further cause the processor to: receive an indication, via an input device, the assessment button was clicked; and generate a fifth GUI component comprising an indication of the distal bracket, the proximal bracket, a minimum region, a vessel profile view and a mirror of the vessel profile view.

Alternatively, or additionally in any of the embodiments of an at least one machine readable storage device above, the vessel profile view can comprise an indication of a border of the vessel and a border of a lumen within the vessel represented along a longitudinal axis of the vessel.

Alternatively, or additionally in any of the embodiments of an at least one machine readable storage device above, the instructions in response to being executed by the processor can further cause the processor to: receive an indication of the vessel border and the lumen border for each of the plurality of frames; generate a graphical representation of the border of the vessel and the border of the lumen based on the indication; generate the profile view comprising the graphical representation of the border of the vessel and the border of the lumen; and mirror the vessel profile view about a central longitudinal axis to generate the mirror of the vessel profile view.

Alternatively, or additionally in any of the embodiments of an at least one machine readable storage device above, the instructions in response to being executed by the processor can further cause the processor to: receive, from a machine learning automated border detection model, the indication of the vessel border and the lumen border: receive an indication of a confidence of the vessel border for each of the plurality of frames; determine, for each of the plurality of frames, whether the confidence is less than or equal to a threshold confidence level; and generate the graphical representation of the vessel border for a first portion of the central longitudinal axis comprising a first graphical representation based on a determination that the confidence is less than or equal to the threshold for the plurality of frames associated with the first portion; and generate the graphical representation of the vessel border for a second portion of the central longitudinal axis comprising a second graphical representation based on a determination that the confidence is not less than or equal to the threshold for the plurality of frames associated with the second portion, wherein the second graphical representation is different than the first graphical representation.

Alternatively, or additionally in any of the embodiments of an at least one machine readable storage device above, the first graphical representation can comprise a first color, first width, or first style of line and wherein the second graphical representation comprises a second color, second width, or second style of line.

BRIEF DESCRIPTION OF THE SEVERAL VIEWS OF THE DRAWINGS

To easily identify the discussion of any element or act, the most significant digit or digits in a reference number refer to the figure number in which that element is first introduced.

FIG. 3B illustrates a cross-section view of a frame of IVUS images.

FIG. 17 illustrates a logic flow for generating a graphical interface for an IVUS imaging system.

DETAILED DESCRIPTION

The foregoing has broadly outlined the features and technical advantages of the present disclosure such that the following detailed description of the disclosure may be better understood. It is to be appreciated by those skilled in the art that the embodiments disclosed may be readily utilized as a basis for modifying or designing other structures for carrying out the same purposes of the present disclosure. The novel features of the disclosure, both as to its organization and operation, together with further objects and advantages will be better understood from the following description when considered in connection with the accompanying figures. It is to be expressly understood, however, that each of the figures is provided for the purpose of illustration and description and is not intended as a definition of the limits of the present disclosure.

As noted, the present disclosure relates to IVUS systems and automatic assessment of the IVUS images. In particular, the disclosure provides a graphical user interface (GUI) arranged to convey information related to the IVUS images and lesion assessment and provide for the user to manipulate the information. As such, an example IVUS imaging system, patient vessel, and series of IVUS images are described.

Suitable IVUS imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,246,959; 7,306,561; and 6,945,938; as well as U.S. Patent Application Publication Numbers 2006/0100522; 2006/0106320; 2006/0173350; 2006/0253028; 2007/0016054; and 2007/0038111; all of which are incorporated herein by reference.

Figure 1:
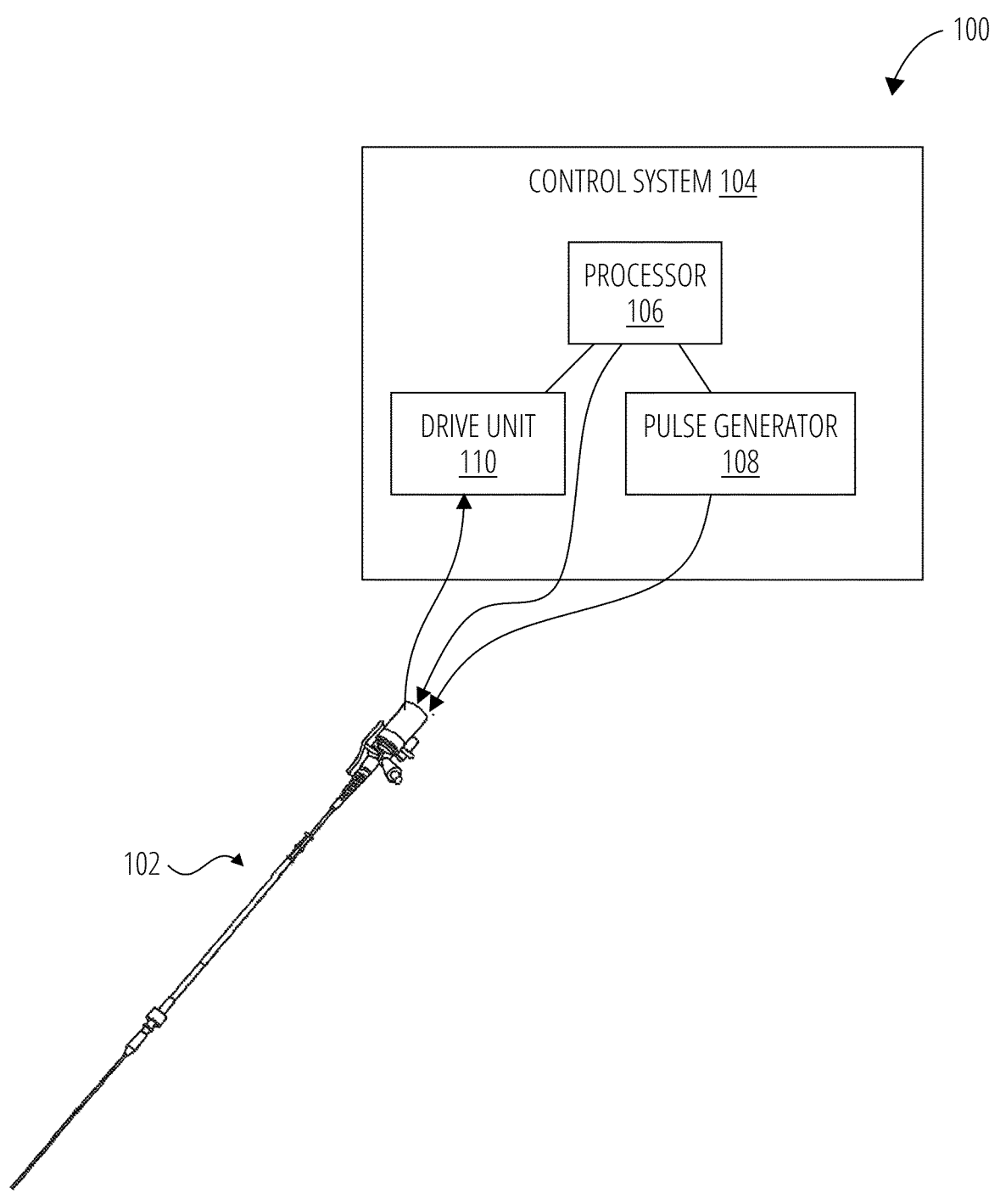
FIG. 1 illustrates a IVUS imaging system.

FIG. 1 illustrates one embodiment of an IVUS imaging system 100. The IVUS imaging system 100 includes a catheter 102 that is couplable to a control system 104. The control system 104 may include, for example, a processor 106, a pulse generator 108, and a drive unit 110. The pulse generator 108 forms electric pulses that may be input to one or more transducers (not shown) disposed in the catheter 102.

With some embodiments, mechanical energy from the drive unit 110 can be used to drive an imaging core (also not shown) disposed in the catheter 102. In at least some embodiments, electric signals transmitted from the one or more transducers may be input to the processor 106 for processing. In at least some embodiments, the processed electric signals from the one or more transducers can be used to form a series of images, described in more detail below. For example, a scan converter can be used to map scan line samples (e.g., radial scan line samples, or the like) to a two-dimensional Cartesian grid, which can be used as the basis for a series of IVUS images that can be displayed for a user.

In at least some embodiments, the processor 106 may also be used to control the functioning of one or more of the other components of the control system 104. For example, the processor 106 may be used to control at least one of the frequency or duration of the electrical pulses transmitted from the pulse generator 108, the rotation rate of the imaging core by the drive unit 110. Additionally, where IVUS imaging system 100 is configured for automatic pullback, the drive unit 110 can control the velocity and/or length of the pullback.

Figure 2:
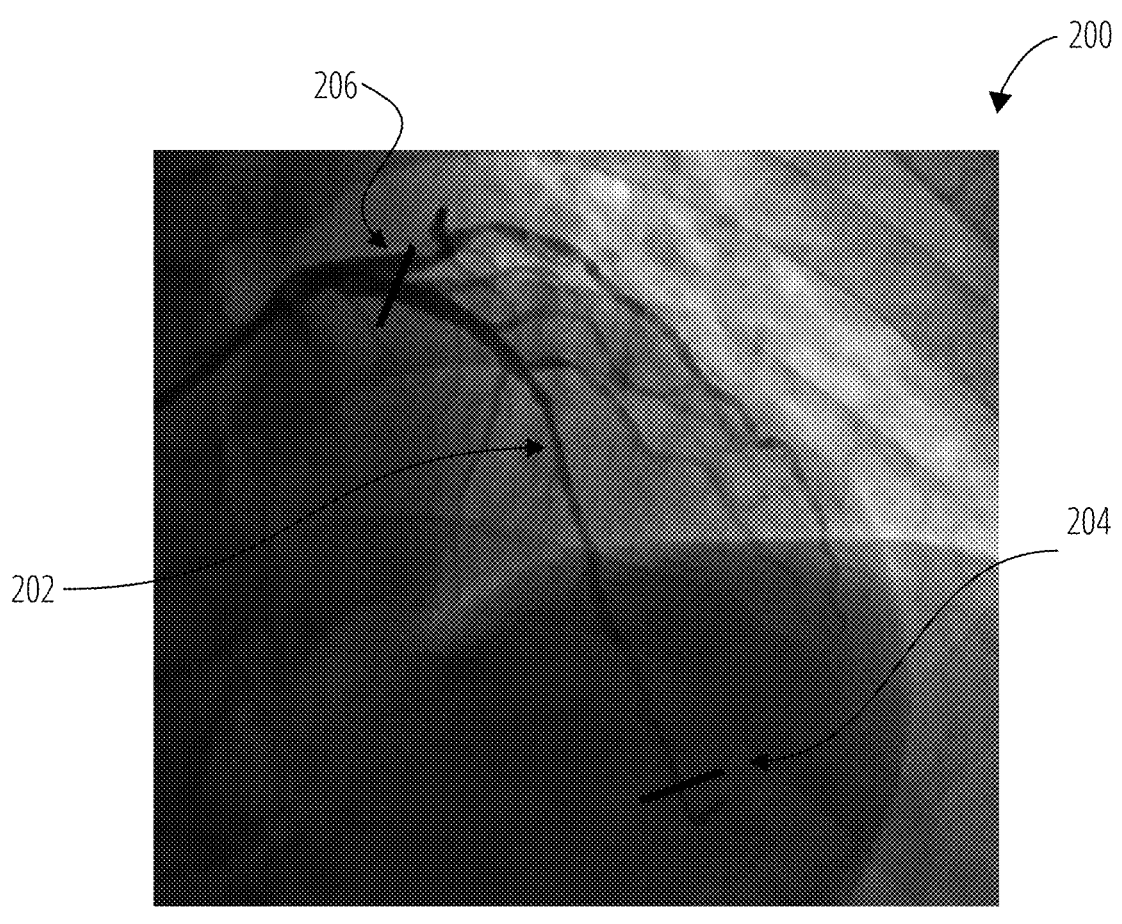
FIG. 2 illustrates an angiographic image of a vessel.

FIG. 2 illustrates an image 200 of a vessel 202 of a patient. As described, IVUS imaging systems (e.g., IVUS imaging system 100, or the like) are used to capture a series of images or a "recording" or a vessel, such as, vessel 202. For example, an IVUS catheter (e.g., catheter 102) is inserted into vessel 202 and a recording, or a series of IVUS images, is captured as the catheter 102 is pulled back from a distal end 204 to a proximal end 206. The catheter 102 can be pulled back manually or automatically (e.g., under control of drive unit 110, or the like).

Figure 3A:
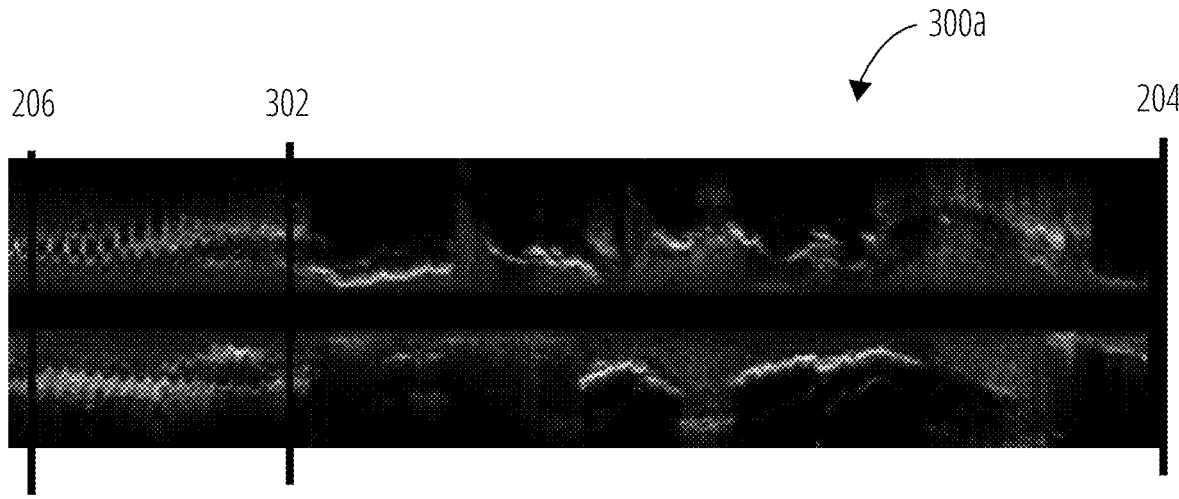
FIG. 3A illustrates a longitudinal view of IVUS images.

FIG. 3A and FIG. 3B illustrates two-dimensional (2D) representations of IVUS images of vessel 202. For example, FIG. 3A illustrates IVUS images 300a depicting a longitudinal view of the IVUS recording of vessel 202 between proximal end 206 and distal end 204.

FIG. 3B illustrates an image frame 300b depicting an on-axis (or short axis, or cross-section) view of vessel 202 at point 302. Said differently, image frame 300b is a single frame or single image from a series of IVUS images that can be captured between distal end 204 and proximal end 206 as described herein. As introduced above, the present disclosure provides systems and techniques to process raw IVUS images to identify regions of interest, such as, for example starting and ending points between which include frames of interest in a series of IVUS images.

For example, IVUS images 300a depicts an entire series of IVUS images taken of vessel 202 between distal end 204 and proximal end 206. IVUS images may be captured at several stages of a percutaneous coronary intervention (PCI). That is, IVUS may be employed pre-PCI, peri-PCI, or post-PCI. For example, IVUS may be employed to capture images of the state of the vessel 202 before a stent is implanted. In such an example, automatic assessments of the images can be performed (e.g., vessel border detection, lumen border detection, plaque burden detection, key frame identification, stent size and landing zone recommendations, stent expansion estimation, or the like). It is to be appreciated that this is a significant amount of information to convey to a user. Further, conveying this information along with the IVUS images (e.g., IVUS images 300a and 300b) in a manner that allows the user to manipulate the automatic assessments (e.g., key frames, or the like) is not provided in the prior art. Thus, the present disclosure provides an advantage in that the improved GUI provides to greater understanding and allows manipulation of the features of the image.

Figure 4:
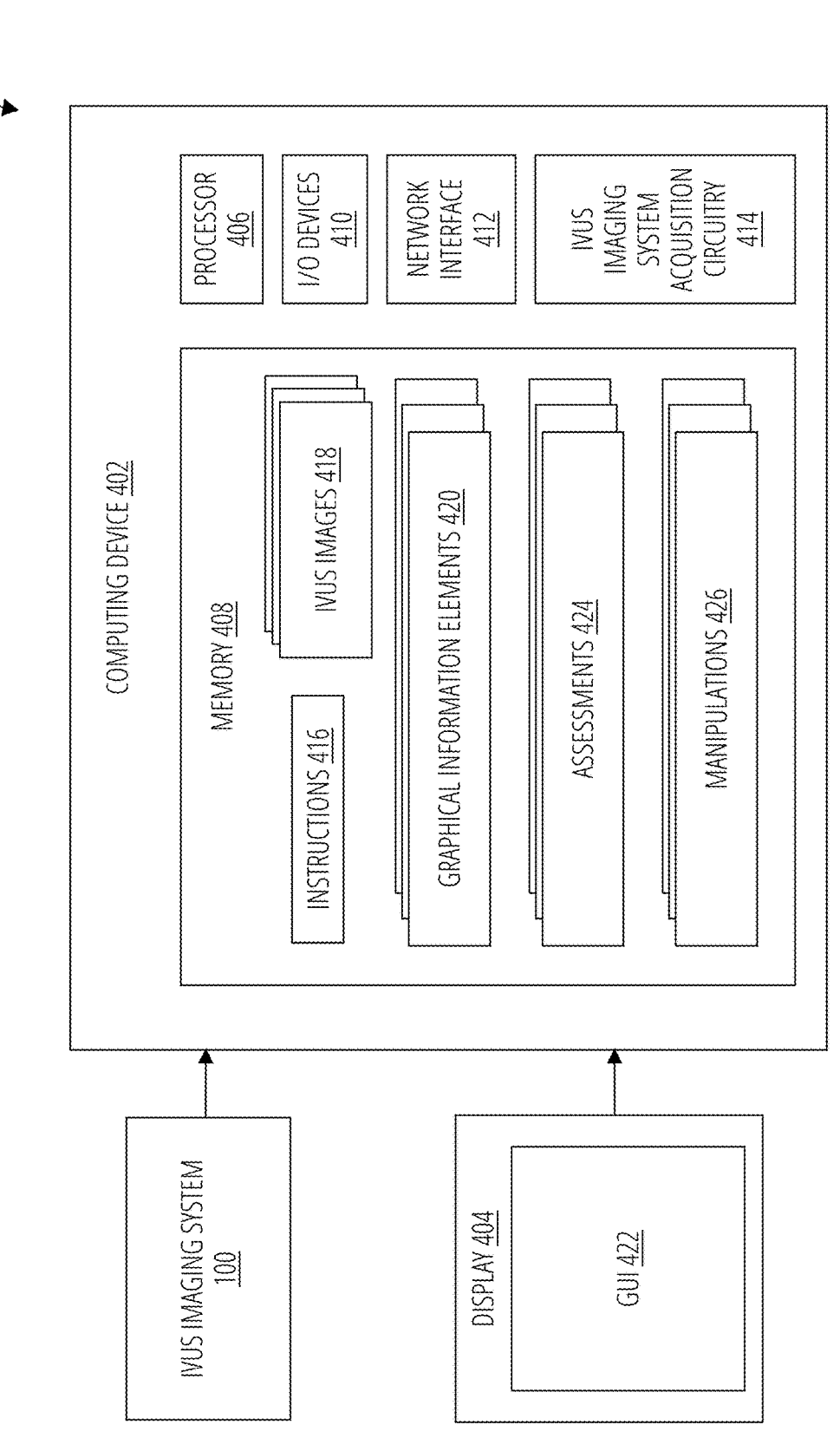
FIG. 4 illustrates IVUS image visualization system.

FIG. 4 illustrates an IVUS images visualization system 400, according to some embodiments of the present disclosure. In general, IVUS images visualization system 400 is a system for processing, annotating, and presenting IVUS images.

IVUS images visualization system 400 can be implemented in a commercial IVUS guidance or navigation system, such as, for example, the AVVIGO® Guidance System available from Boston Scientific®. The present disclosure provides advantages over prior or conventional IVUS navigation systems in that the improved GUI will reduce the time needed for patients to be in treatment. For example, the present disclosure can be implemented in an IVUS navigation system to efficiently communicate IVUS information to a user and allow the user to manipulate the information.

With some embodiments, IVUS images visualization system 400 could be implemented as part of control system 104. Alternatively, control system 104 could be implemented as part of IVUS images visualization system 400. As depicted, IVUS images visualization system 400 includes a computing device 402. Optionally, IVUS images visualization system 400 includes IVUS imaging system 100 and display 404.

Computing device 402 can be any of a variety of computing devices. In some embodiments, computing device 402 can be incorporated into and/or implemented by a console of display 404. With some embodiments, computing device 402 can be a workstation or server communicatively coupled to IVUS imaging system 100 and/or display 404. With still other embodiments, computing device 402 can be provided by a cloud based computing device, such as, by a computing as a service system accessibly over a network (e.g., the Internet, an intranet, a wide area network, or the like). Computing device 402 can include processor 406, memory 408, input and/or output (I/O) devices 410, network interface 412, and IVUS imaging system acquisition circuitry 414.

The processor 406 may include circuitry or processor logic, such as, for example, any of a variety of commercial processors. In some examples, processor 406 may include multiple processors, a multi-threaded processor, a multi-core processor (whether the multiple cores coexist on the same or separate dies), and/or a multi-processor architecture of some other variety by which multiple physically separate processors are in some way linked. Additionally, in some examples, the processor 406 may include graphics processing portions and may include dedicated memory, multiple-threaded processing and/or some other parallel processing capability. In some examples, the processor 406 may be an application specific integrated circuit (ASIC) or a field programmable integrated circuit (FPGA).

The memory 408 may include logic, a portion of which includes arrays of integrated circuits, forming non-volatile memory to persistently store data or a combination of non-volatile memory and volatile memory. It is to be appreciated, that the memory 408 may be based on any of a variety of technologies. In particular, the arrays of integrated circuits included in memory 120 may be arranged to form one or more types of memory, such as, for example, dynamic random access memory (DRAM), NAND memory, NOR memory, or the like.

I/O devices 410 can be any of a variety of devices to receive input and/or provide output. For example, I/O devices 410 can include, a keyboard, a mouse, a joystick, a foot pedal, a display, a touch enabled display, a haptic feedback device, an LED, or the like.

Network interface 412 can include logic and/or features to support a communication interface. For example, network interface 412 may include one or more interfaces that operate according to various communication protocols or standards to communicate over direct or network communication links. Direct communications may occur via use of communication protocols or standards described in one or more industry standards (including progenies and variants). For example, network interface 412 may facilitate communication over a bus, such as, for example, peripheral component interconnect express (PCIe), non-volatile memory express (NVMe), universal serial bus (USB), system management bus (SMBus), SAS (e.g., serial attached small computer system interface (SCSI)) interfaces, serial AT attachment (SATA) interfaces, or the like. Additionally, network interface 412 can include logic and/or features to enable communication over a variety of wired or wireless network standards (e.g., 802.11 communication standards). For example, network interface 412 may be arranged to support wired communication protocols or standards, such as, Ethernet, or the like. As another example, network interface 412 may be arranged to support wireless communication protocols or standards, such as, for example, Wi-Fi, Bluetooth, ZigBee, LTE, 5G, or the like.

The IVUS imaging system acquisition circuitry 414 may include circuitry including custom manufactured or specially programmed circuitry configured to receive or receive and send signals between IVUS imaging system 100 including indications of an IVUS run, a series of IVUS images, or a frame or frames of IVUS images.

Memory 408 can include instructions 416. During operation processor 406 can execute instructions 416 to cause computing device 402 to receive (e.g., from IVUS imaging system 100, or the like) a recording of an "IVUS run" and store the recording as IVUS images 418 in memory 408. For example, processor 406 can execute instructions 416 to receive information elements from IVUS imaging system 100 comprising indications of IVUS images captured by catheter 102 while being pulled back from distal end 204 to proximal end 206, which images comprising indications of the anatomy and/or structure of vessel 202 including vessel walls and plaque. It is to be appreciated that IVUS images 418 can be stored in a variety of image formats or even non-image formats or data structures that comprise indications of vessel 202. Further, IVUS images 418 includes several "frames" or individual images that, when represented co-linearly can be used to form an image of the vessel 202, such as, for example, as represented by IVUS images 300*a* and/or 300*b*.

The present disclosure provides to generate graphical information elements 420 from IVUS images 418 and to generate a GUI 422 to be displayed on display 404 based on the graphical information elements 420. Processor 406 can further be configured to execute instructions 416 to generate assessments 424 based on IVUS images 418. This will be described in greater detail below. However, in general, the assessments can include vessel boundary detection, lumen boundary detection, plaque burden determination, key frame identification, distances between key frames, among other assessments. As such, in some embodiments, graphical information elements 420 can be generated based on IVUS images 418 and assessments 424.

Additionally, processor 406 can be configured to execute instructions 416 to receive manipulations 426 including modifications to assessments 424. For example, processor 406 can execute instructions 416 to receive modifications to vessel and/or lumen boundaries, key frame locations, or the like and store such modifications as manipulations 426. Responsive to receiving manipulations 426, processor 406 can execute instructions 416 to regenerate graphical information elements 420 based on IVUS images 418, assessments 424, and/or manipulations 426.

Figure 5A:
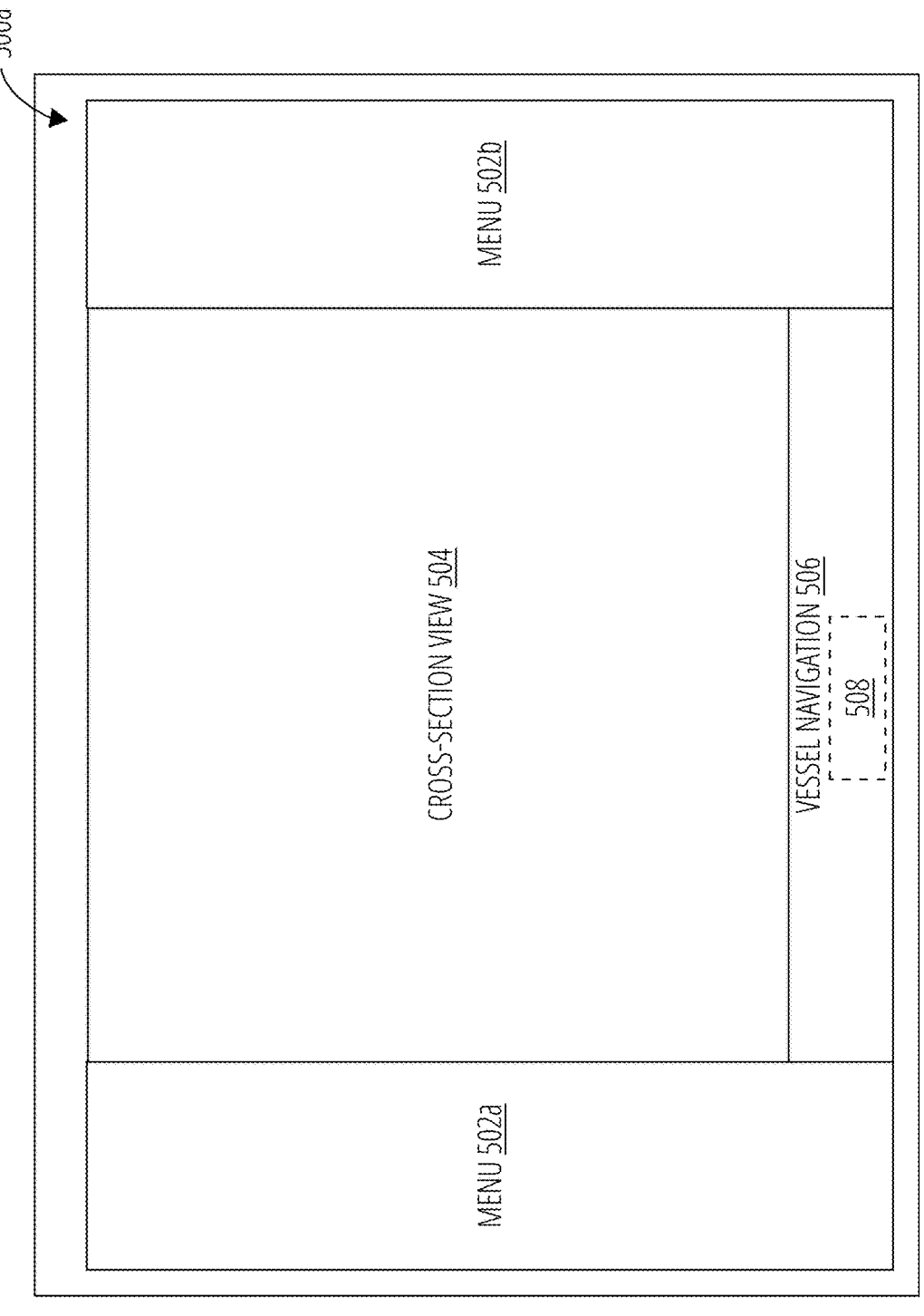
FIG. 5A illustrates a first graphical interface for an IVUS imaging system.

FIG. 5A illustrates a GUI 500*a*, which can be generated according to some embodiments of the present disclosure. For example, GUI 500*a* can be generated by IVUS images visualization system 400 as GUI 422 and displayed on display 404. As depicted, GUI 500*a* includes several graphical information elements 420, such as, menus 502*a* and 502*b*, cross-section view 504, and vessel navigation 506. Further, vessel navigation 506 includes single frame ALA button 508. With some embodiments, processor 406 can be configured to execute instructions 416 to generate GUI 500*a* once a IVUS recording (or IVUS run) is complete. For example, responsive to receiving IVUS images 418, processor 406 can execute instructions 416 to generate GUI 500*a*. Of note, GUI 500*a* does not include graphical information elements 420 having indications of assessments 424. For example, assessments 424 (e.g., automatic lesion assessment outputs like vessel and lumen borders, key frames, and the like) are not displayed until the user selects (e.g., activates, clicks, or the like) single frame ALA button 508. As such, GUI 500*a* provides the user with as unobstructed and large a view as possible of the cross-section view 504 of IVUS images 418.

Menu 502*a* can comprise GUI inputs such as button, drop down menus, selection icons, or the like. Menu 502*a* can include GUI input options to select measurement and annotation tools, length tools, modification reset buttons, or the like. Menu 502*b* can comprise GUI inputs such as buttons, drop down menus, selection icons, or the like. Menu 502*b* can include GUI inputs options to select views related to views of the IVUS images, layout options, annotations, navigation, dynamic review options, status of the computing device, or the like.

Cross-section view 504 can comprise a cross-sectional view of a one (e.g., a frame, or the like) of IVUS images 418. For example, cross-section view 504 can include image frame 300*b*. Examples of vessel navigation 506 are provided below. However, in general, vessel navigation 506 can include a navigation slider to navigation through IVUS images 418, which is linked to the 504. That is, as the slider is moved the image displayed in cross-section view 504 changes to match the location indicated by the slider. Further with some examples, the location of distal and proximal frames (e.g., distal and proximal key frames) linearly along the series of IVUS images 418 is indicated (e.g., with brackets, or the like). Further, vessel navigation 506 can include a single frame ALA button 508. These and other embodiments of vessel navigation 506 are described below.

Figure 5B:
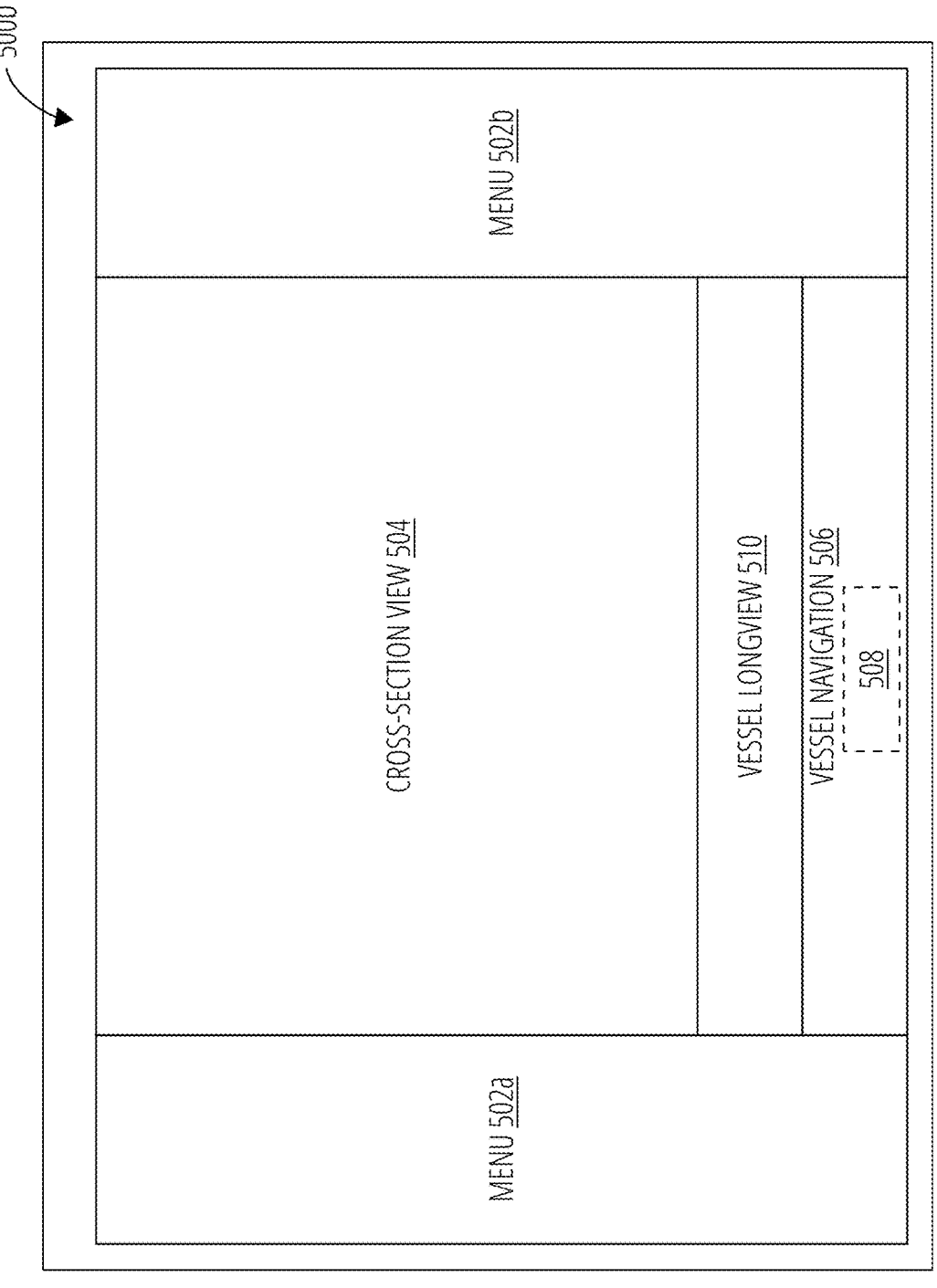
FIG. 5B illustrates a second graphical interface for an IVUS imaging system.

FIG. 5B illustrates a GUI 500*b*, which can be generated according to some embodiments of the present disclosure. For example, GUI 500*b* can be generated by IVUS images visualization system 400 as GUI 422 and displayed on display 404. As depicted, GUI 500*b* includes several graphical information elements 420 like GUI 500*a*. Notably, GUI 500*b* further includes vessel long view 510. Vessel Longview 510 can comprise a longitudinal view of the vessel (e.g., vessel 202) represented by the IVUS images 418. For example, vessel long view 510 can include IVUS images 300*a*.

Figure 5C:
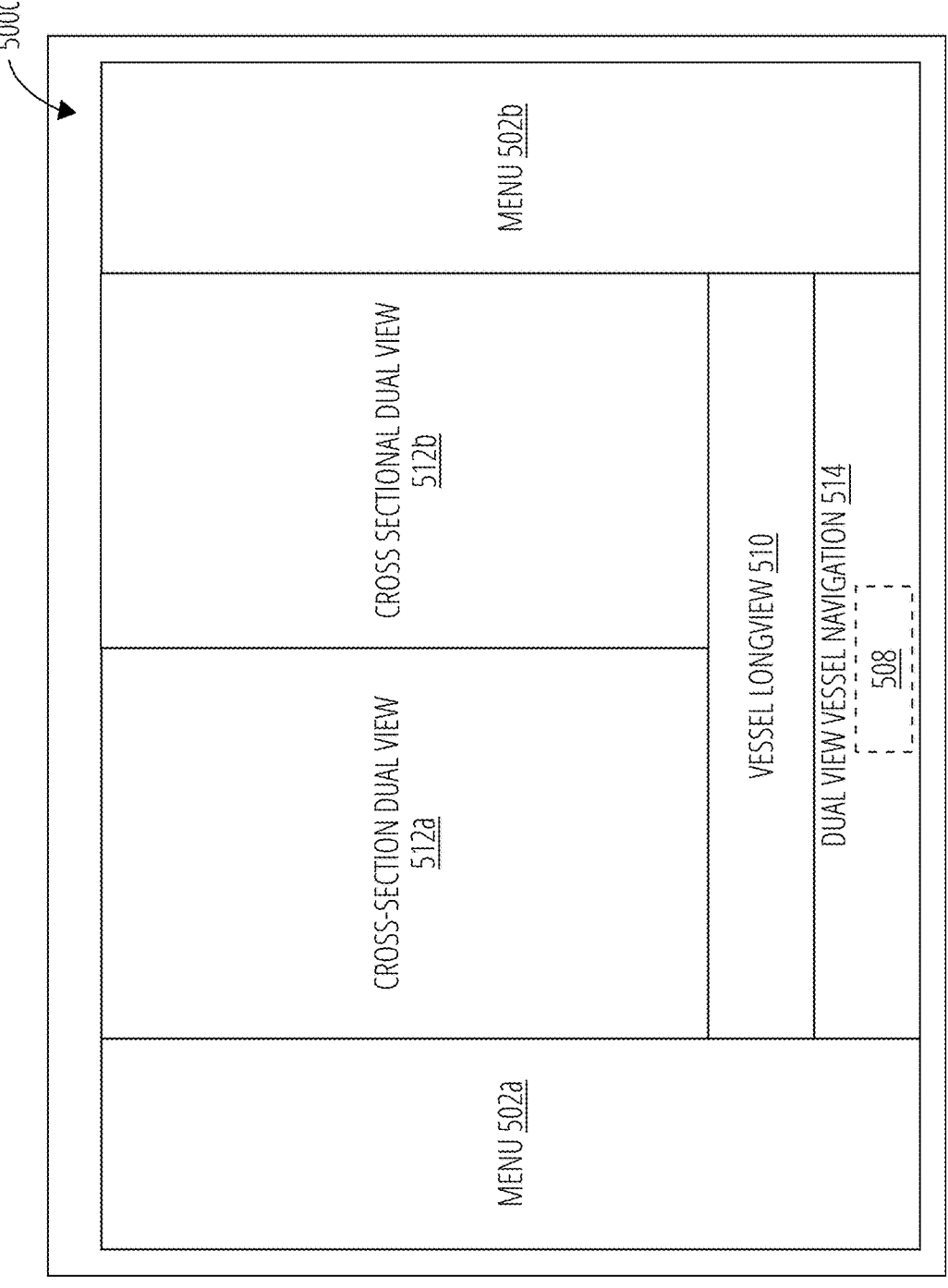
FIG. 5C illustrates a third graphical interface for an IVUS imaging system.

FIG. 5C illustrates a GUI 500*c*, which can be generated according to some embodiments of the present disclosure. For example, GUI 500*c* can be generated by IVUS images visualization system 400 as GUI 422 and displayed on display 404. As depicted, GUI 500*c* includes several graphical information elements 420 like GUI 500*a* and GUI 500*b*. Notably, GUI 500*c* includes multiple cross-section views. GUI 500*c* includes cross-section dual view 512*a* and cross sectional dual view 512*b* side by side. Cross-section dual views 512*a* and 512*b* can be like cross-section view 504 and include a cross-sectional view of a one (e.g., a frame, or the like) of IVUS images 418. For example, cross-section dual view 512*a* can include an image like image frame 300*b* while cross sectional dual view 512*b* can include an image like image frame 300*b* but from another frame of IVUS images 418. Further, GUI 500*c* may optionally include dual view vessel navigation 514 which includes multiple sliders (described below) providing for navigation and visualization of each of cross-section dual view 512*a* and cross sectional dual view 512*b* longitudinally along IVUS images 418.

Figure 6A:
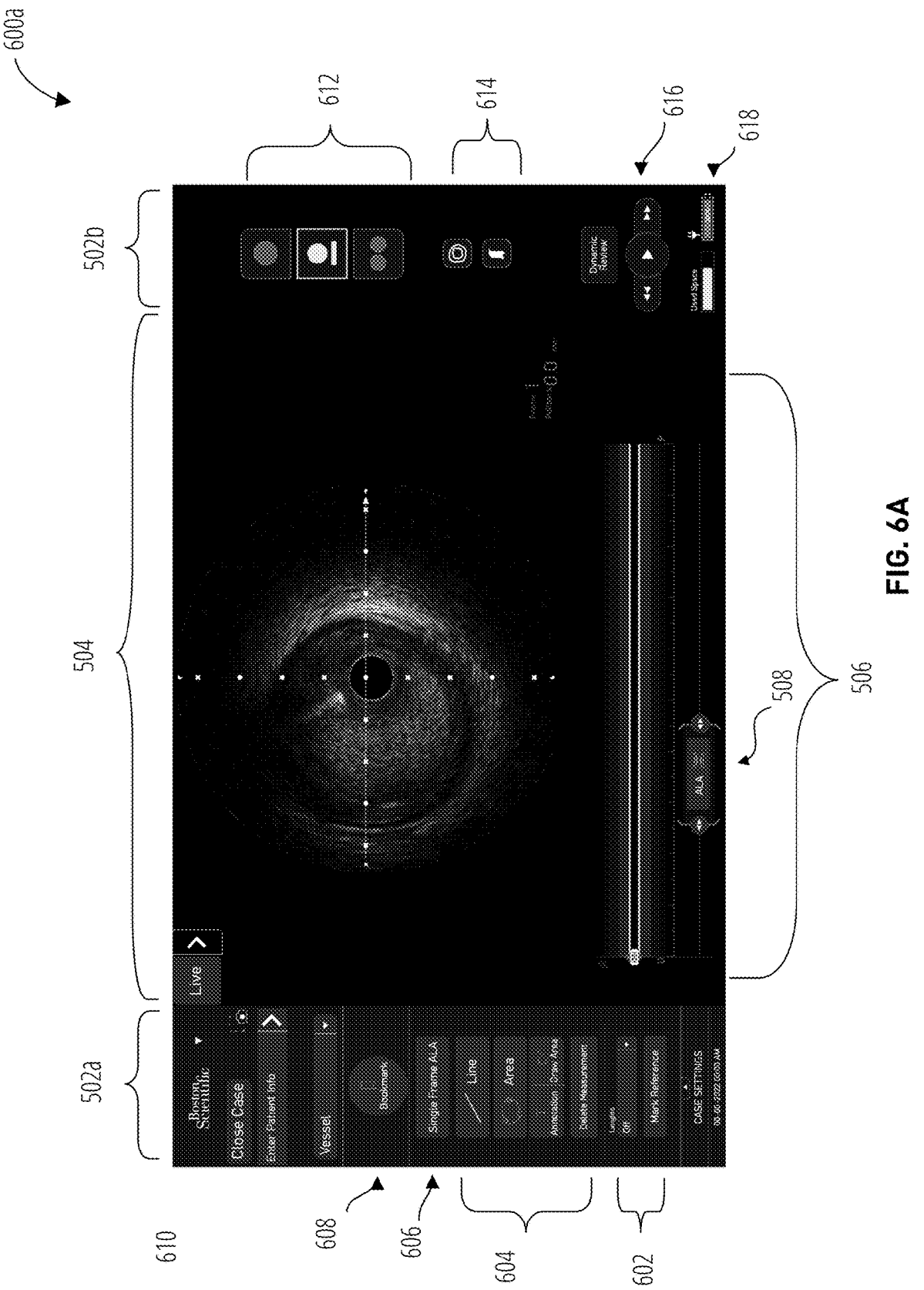
FIG. 6A illustrates a fourth graphical interface for an IVUS imaging system.

FIG. 6A illustrates a GUI 600*a*, which can be generated according to some embodiments of the present disclosure. For example, GUI 600*a* can be generated by IVUS images visualization system 400 as GUI 422 and displayed on display 404.

With some embodiments, responsive to completion of an IVUS recording (e.g., receiving IVUS images 418, or the like) processor 406 can execute instructions 416 to generate graphical information elements 420 and GUI 600*a* from graphical information elements 420.

As depicted, GUI 600*a* includes menu 502*a* and menu 502*b* disposed on either sides of (or framing) cross-section view 504 and vessel navigation 506. GUI 600*a* can include menu 502*a*, which itself includes length measurements inputs 602, measurement and annotation inputs 604, single frame ALA button 606, bookmark button 608, and snapshot button 610. Additionally, GUI 600*a* can include menu 502*b*, which itself includes layout buttons 612, viewing buttons 614, dynamic review navigation 616, and tablet status 618.

With some examples, length measurements inputs 602 can include a drop down menu including options to (1) not show length, (2) show length "between brackets" (e.g., between key frame brackets, or the like), (3) show length "between marks" (e.g., between bookmarks and brackets, or the like), (4) show length "to current frame" (e.g., between scrubber or frame slider indicating current frame location and bookmarks or brackets, or the like), or (5) shows length between dual frames (e.g., discussed in greater detail below). In some examples, measurement and annotation inputs 604 can include multiple dropdown menus and/or buttons arranged to select several options for annotating and/or measuring aspects of the current frame (e.g., lumen or vessel boundaries, or the like) or annotating (e.g., adding text) to the current frame.

The vessel navigation 506 can operate to provide ALA predicted borders on the current frame. If the ALA borders were already showing and had already been manually modified, vessel navigation 506 may operate to resets the borders to the originally predicted borders.

The layout buttons 612 can be configured to change the display framed between the menus 502*a* and 502*b* to be either a singular cross-section view (e.g., cross-section view 504) and the vessel navigation 506, a singular cross-section view (e.g., cross-section view 504) along with a longitudinal view of the vessel (e.g., vessel navigation 506, or the like) and the vessel navigation 506, or a dual cross-section view (described in greater detail below).

Figure 6B:
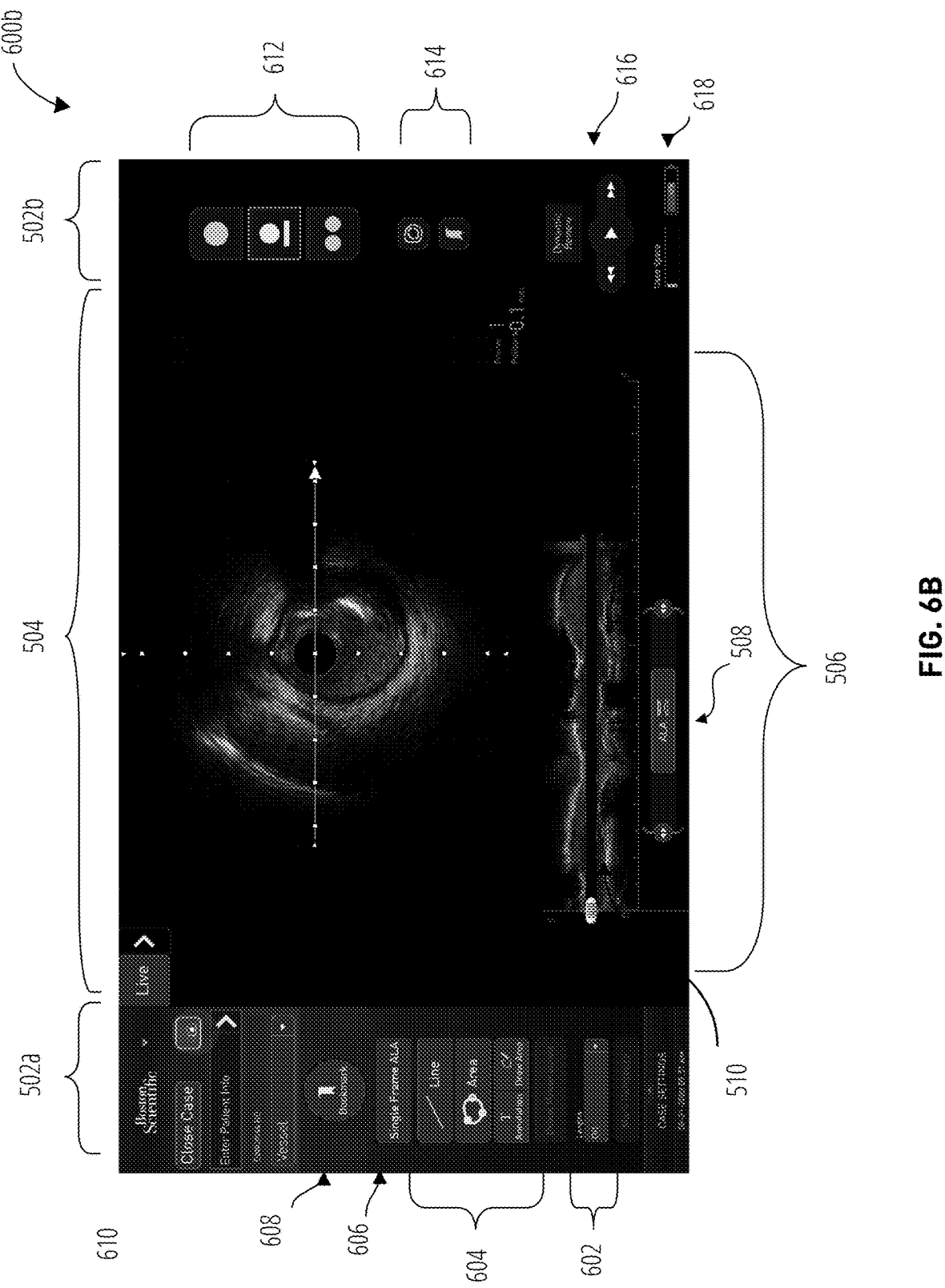
FIG. 6B illustrates a fifth graphical interface for an IVUS imaging system.

FIG. 6B illustrates a GUI 600*b*, which can be generated according to some embodiments of the present disclosure. For example, GUI 600*b* can be generated by IVUS images visualization system 400 as GUI 422 and displayed on display 404.

With some embodiments, responsive to completion of an IVUS recording (e.g., receiving IVUS images 418, or the like) processor 406 can execute instructions 416 to generate graphical information elements 420 and GUI 600*b* from graphical information elements 420.

GUI 600*b* can be like GUI 600*a* with the notable difference that GUI 600*b* includes vessel long view 510. With some embodiments, the GUI 600*b* can be generated responsive to a user selecting the long view layout option in layout buttons 612. As can be seen, the vessel long view 510 include a depiction of the IVUS images 418 longitudinally disposed between the cross-section view 504 and the vessel navigation 506.

Figures 7A, 7B:
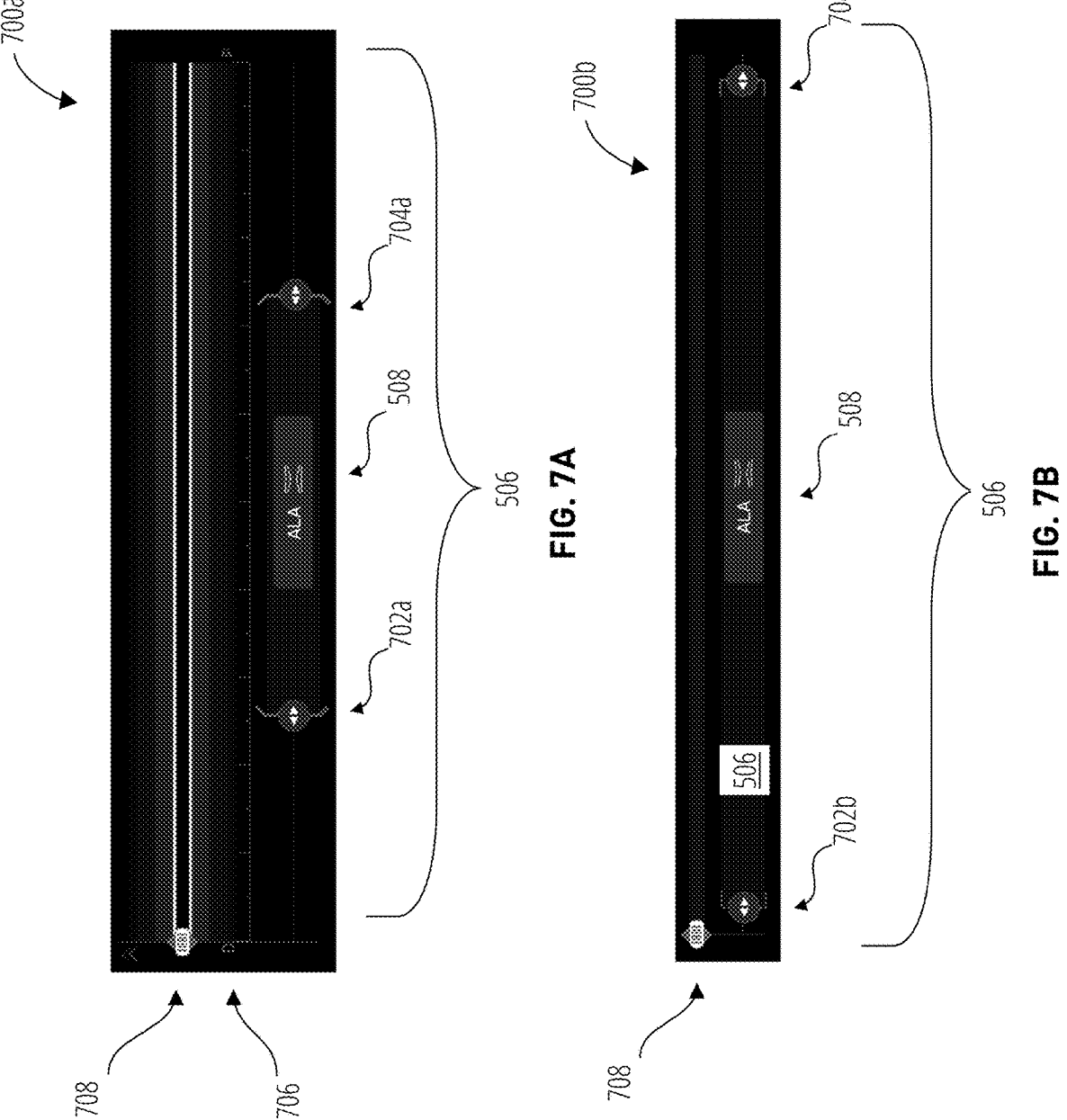
FIG. 7A illustrates a first graphical component of a graphical interface for an IVUS imaging system.
FIG. 7B illustrates a second graphical component of a graphical interface for an IVUS imaging system.

FIG. 7A and FIG. 7B illustrate examples of vessel navigation 506. In some embodiments, processor 406 can execute instructions 416 to generate graphical information elements 420 including indications of vessel navigation 506 depending upon whether the IVUS images 418 are captured via an automatic pullback or a manual pullback. For example, FIG. 7A illustrates vessel navigation 700*a*, according to some embodiments of the present disclosure. IVUS images visualization system 400 can be configured to generate vessel navigation 700*a* as vessel navigation 506 when the IVUS images 418 correspond to an automatic IVUS run. In such an embodiment, processor 406 can execute instructions 416 to generate graphical information elements 420, with which vessel navigation 700*a* can be generated, where vessel navigation 700*a* comprises vessel navigation 506, distal bracket end 704*a*, proximal bracket end 702*a*, single frame ALA button 508, slider axis 706, and view slider 708.

Similarly, FIG. 7B illustrates vessel navigation 700*b*, according to some embodiments of the present disclosure. IVUS images visualization system 400 can be configured to generate vessel navigation 700*b* as vessel navigation 506 when the IVUS images 418 correspond to a manual IVUS run. In such an embodiment, processor 406 can execute instructions 416 to generate graphical information elements 420, with which vessel navigation 700b can be generated, where vessel navigation 700b comprises vessel navigation 506, distal bracket end 704b, proximal bracket end 702b, single frame ALA button 508, and view slider 708.

In general, vessel navigation 700a and vessel navigation 700b are similar except for key distinctions in look and feel to indicate that the IVUS images are from an automatic or a manual pullback operation. For example, proximal bracket end 702a and distal bracket end 704a can comprise angled brackets indicating an automatic pullback for the IVUS images 418 while the proximal bracket end 702b and distal bracket end 704b can comprise 90 degree brackets indicating a manual pullback.

With some embodiments, proximal bracket ends 702a and 702b as well as distal bracket ends 704a and 704b can have an initial position corresponding to distal and proximal key frames (e.g., from an automatic lesion assessment program, or the like). Processor 406 can execute instructions 416 to enable proximal bracket ends 702a and 702b as well as distal bracket ends 704a and 704b to be manipulatable by a user (e.g., via I/O devices 410). For example, a user can drag (e.g., via a touch screen, via a mouse, or the like) one of the brackets to change the position of the key frame represented by the bracket. Processor 406 can execute instructions 416 to, responsive to receiving an indication to change the position, move the view slider 708 to the bracket position and track the movement of the bracket. As such, the cross-section view (and longitudinal view if enabled) will follow the movement of the bracket.

Furthermore, vessel navigation 700a comprises slider axis 706 which can comprise indications (e.g., tick marks or the like) of the distance of the IVUS frames from the distal end (or start of the IVUS run).

FIG. 8A through FIG. 8D illustrate examples of graphical information elements 420 that can be generated to form graphical components of vessel navigation 506. These figures illustrate single frame ALA button 508 and options for the graphical representation of single frame ALA button 508 based on the distance between proximal bracket end 702a and distal bracket end 704a. These figures depict changes to single frame ALA button 508 as the proximal bracket end 702a and distal bracket end 704a are moved (or automatically positioned) as outlined above closer together.

Figures 8A, 8B, 8C, 8D:
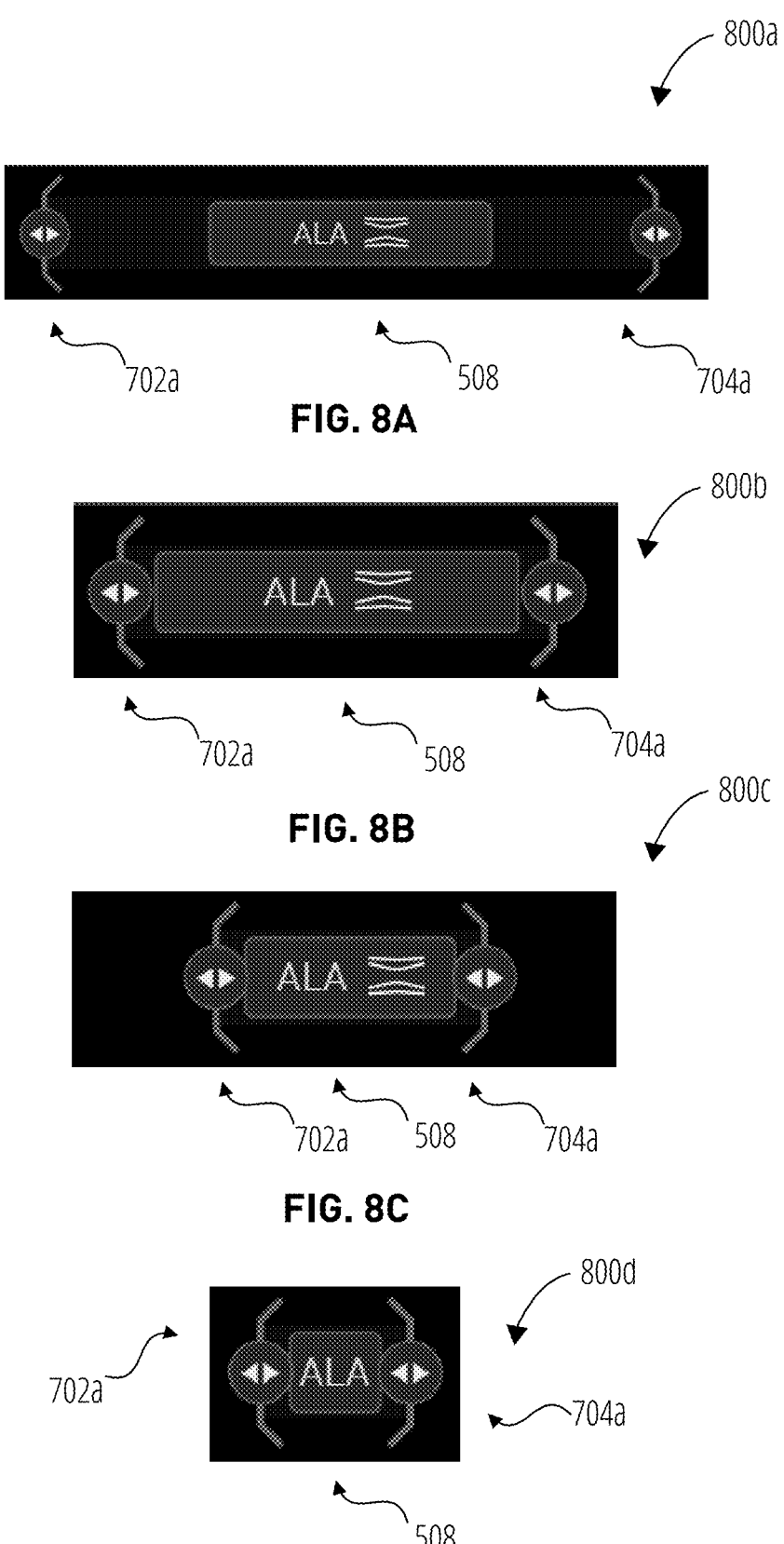
FIGS. 8A, 8B, 8C, and 8D illustrate versions of a third graphical component of a graphical interface for an IVUS imaging system.

FIG. 8A illustrates graphical information elements 800a, according to some embodiments of the present disclosure. Processor 406 can execute instructions 416 to generate graphical information elements 420 comprising indications of representations of graphical information elements 800a including proximal bracket end 702a (or proximal bracket end 702b), distal bracket end 704a (or distal bracket end 704b), and single frame ALA button 508. With some embodiments, processor 406 can execute instructions 416 to determine a distance between the brackets and can select the graphical representation for 508 based on the determined distance. For example, where the distance is greater than a threshold, processor 406 can execute instructions 416 to select single frame ALA button 508 comprising graphical representations of text and an icon.

FIG. 8B and FIG. 8C illustrate graphical information elements 800b and graphical information elements 800c respectively. Processor 406 can execute instructions 416 to generate graphical information elements 420 comprising indications of representations of graphical information elements 800b or graphical information elements 800c including proximal bracket end 702a (or proximal bracket end 702b), distal bracket end 704a (or distal bracket end 704b), and single frame ALA button 508. With some embodiments, processor 406 can execute instructions 416 to determine a distance between the brackets and can select the graphical representation for 508 based on the determined distance. For example, where the distance is greater than a threshold, processor 406 can execute instructions 416 to select single frame ALA button 508 comprising graphical representations of text and an icon.

FIG. 8D illustrates graphical information elements 800d, according to some embodiments of the present disclosure. Processor 406 can execute instructions 416 to generate graphical information elements 420 comprising indications of representations of graphical information elements 800d including proximal bracket end 702a (or proximal bracket end 702b), distal bracket end 704a (or distal bracket end 704b), and single frame ALA button 508. With some embodiments, processor 406 can execute instructions 416 to determine a distance between the brackets and can select the graphical representation for 508 based on the determined distance. For example, where the distance is less than (or less than or equal to) a threshold, processor 406 can execute instructions 416 to select single frame ALA button 508 comprising graphical representations of text (or an icon) but not both.

Figure 9A:
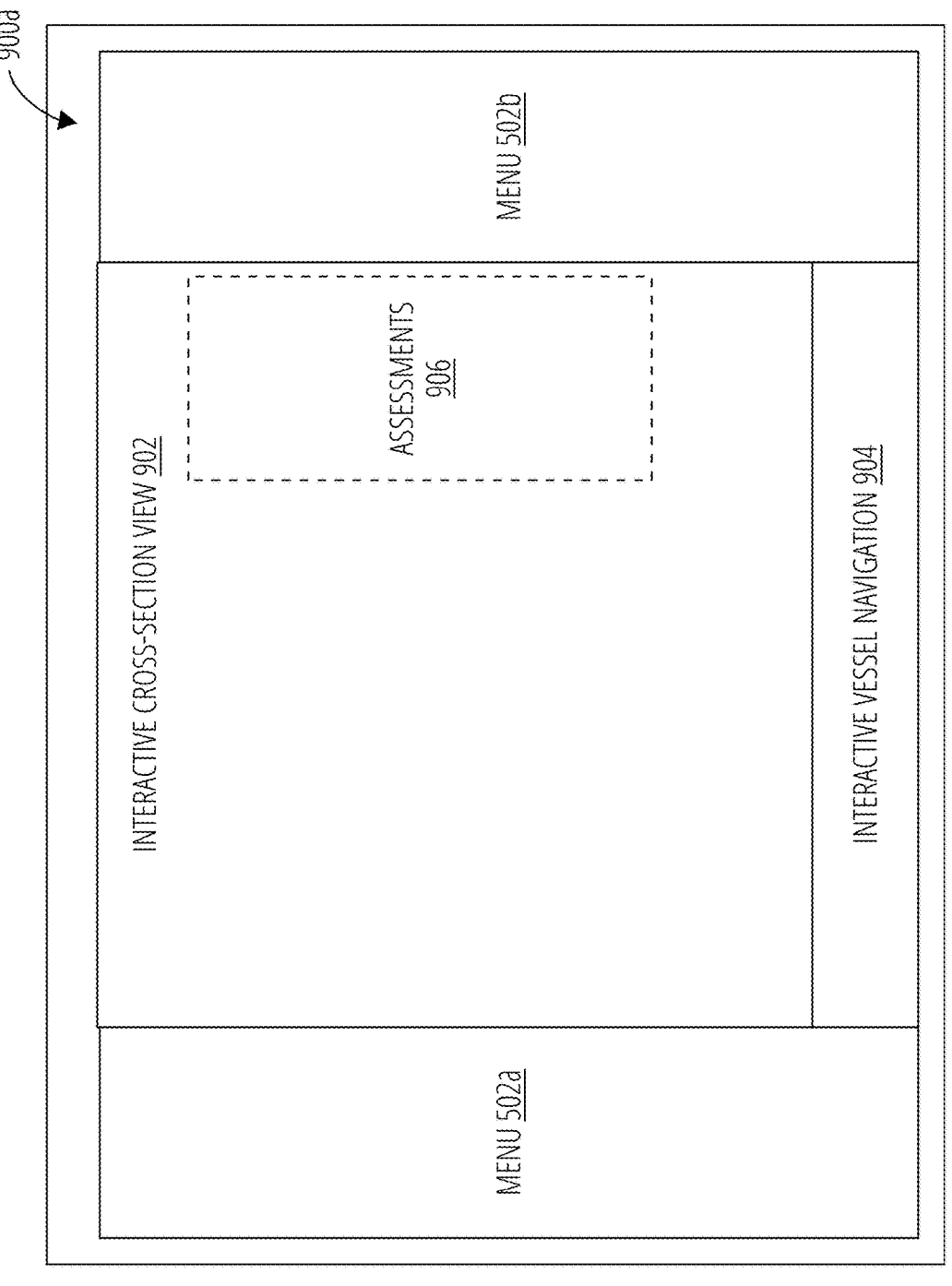
FIG. 9A illustrates a sixth graphical interface for an IVUS imaging system.

FIG. 9A illustrates a GUI 900a, which can be generated according to some embodiments of the present disclosure. For example, GUI 900a can be generated by IVUS images visualization system 400 as GUI 422 and displayed on display 404. As depicted, GUI 900a includes several graphical information elements 420, such as, menus 502a and 502b, interactive cross-section view 902, and interactive vessel navigation 904. With some embodiments, processor 406 can be configured to execute instructions 416 to generate GUI 900a once vessel navigation 506 is selected. For example, responsive to receiving input (e.g., via I/O devices 410, or the like) indicating that vessel navigation 506 is selected, processor 406 can execute instructions 416 to generate GUI 900a. With some embodiments, processor 406 can execute instructions 416 to change (or replace) portions of a prior GUI (e.g., GUI 500a, GUI 500b, etc.) with interactive portions as depicted in FIG. 9A.

For example, cross-section view 504 can be replaced with interactive cross-section view 902. Examples of interactive cross-section view 902 are given in greater detail below. However, in general, interactive cross-section view 902 can include a representation of image frame 300b and assessments 906 as well as indications of vessel and lumen borders. Similarly, vessel navigation 506 can be replaced with 904. Examples of interactive vessel navigation 904 are given in greater detail below. However, in general, interactive vessel navigation 904 can include representations of a vessel and lumen profile as well as an indication of a minimum region. Examples of assessments 906 are given in greater detail below. However, in general, they are based on assessments 424.

Figure 9B:
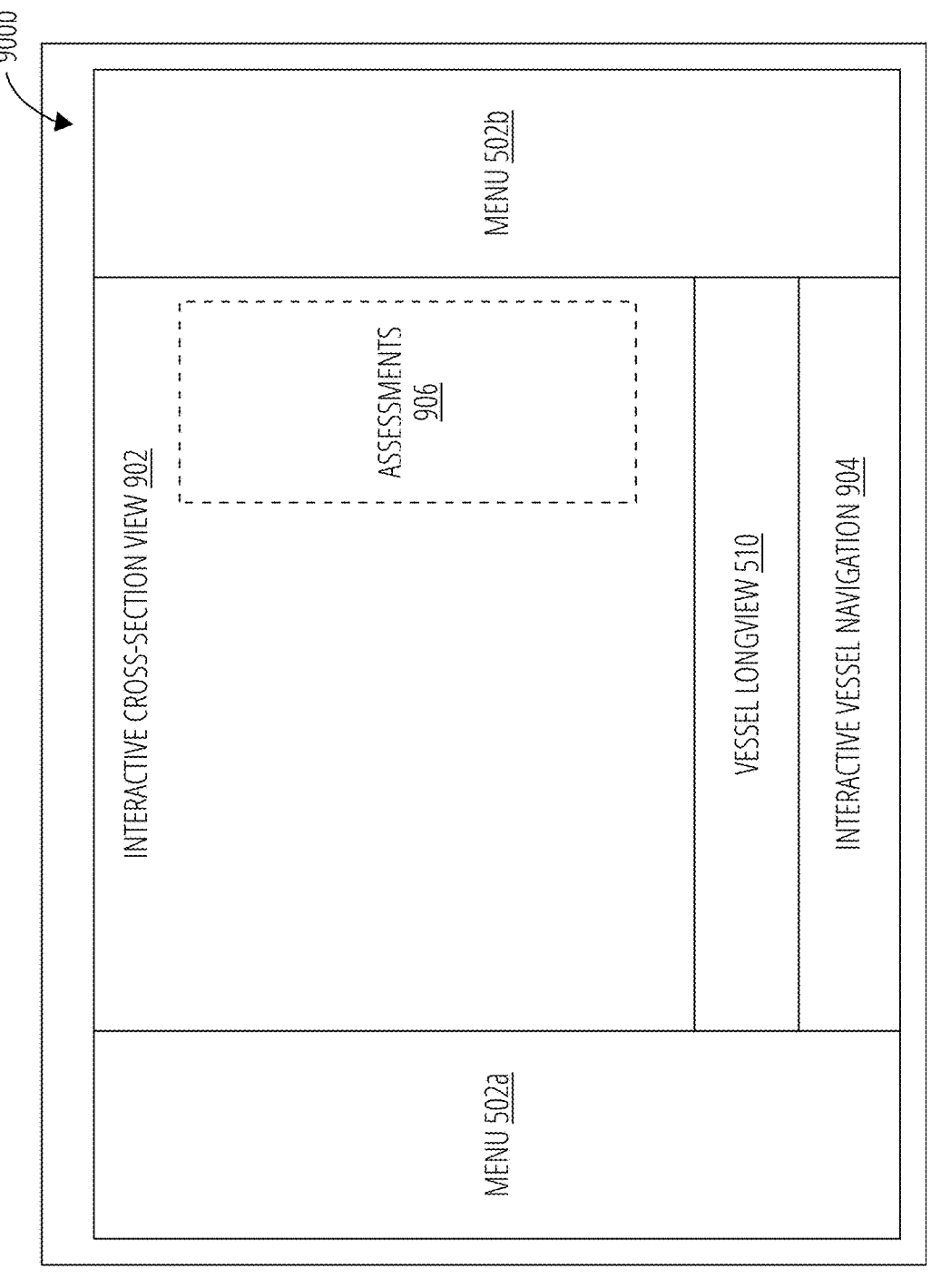
FIG. 9B illustrates a seventh graphical interface for an IVUS imaging system.

FIG. 9B illustrates a GUI 900b, which can be generated according to some embodiments of the present disclosure. For example, GUI 900b can be generated by IVUS images visualization system 400 as GUI 422 and displayed on display 404. As depicted, GUI 900b includes several graphical information elements 420 like GUI 900a. Notably, GUI 900b further includes vessel long view 510. Vessel long view 510 can comprise a longitudinal view of the vessel (e.g., vessel 202) represented by the IVUS images 418. For example, vessel long view 510 can include IVUS images 300a.

Figure 10:
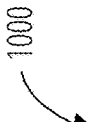
FIG. 10 illustrates an eighth graphical interface for an IVUS imaging system.

FIG. 10 illustrates a GUI 1000, which can be generated according to some embodiments of the present disclosure. For example, GUI 1000 can be generated by IVUS images visualization system 400 as GUI 422 and displayed on display 404. With some embodiments, responsive to activation of the vessel navigation 506, processor 406 can execute instructions 416 to generate graphical information elements 420 and GUI 1000 from graphical information elements 420.

As depicted, GUI 1000 includes menu 502a and menu 502b disposed on either sides of (or framing) interactive cross-section view 902 and interactive vessel navigation 904. Interactive cross-section view 902 includes depictions of a frame of IVUS images 418 (not depicted for clarity) and graphical representations of borders 1002 associated with the frame of the IVUS images 418 corresponding to the location with which view slider 708 is disposed as well as depictions or representations of assessments 906.

Additionally, interactive vessel navigation 904 includes proximal bracket end 702a, distal bracket end 704a, view slider (not numbered), profile view 1004, and minimum region 1006. Examples of profile view 1004 and minimum region 1006 are given below.

Figure 11A:
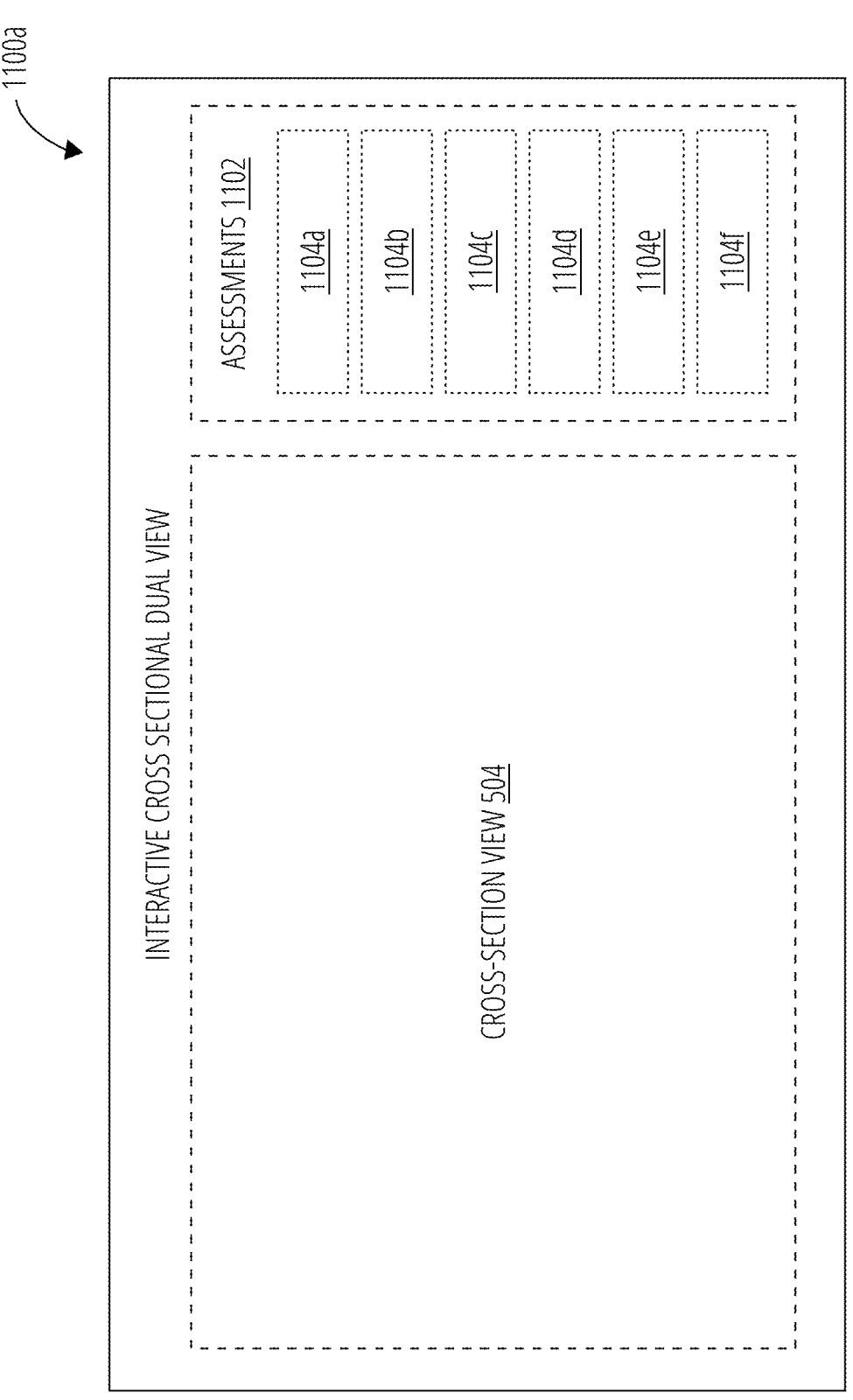
FIG. 11A illustrates a third graphical component of a graphical interface for an IVUS imaging system.
Figure 11B:
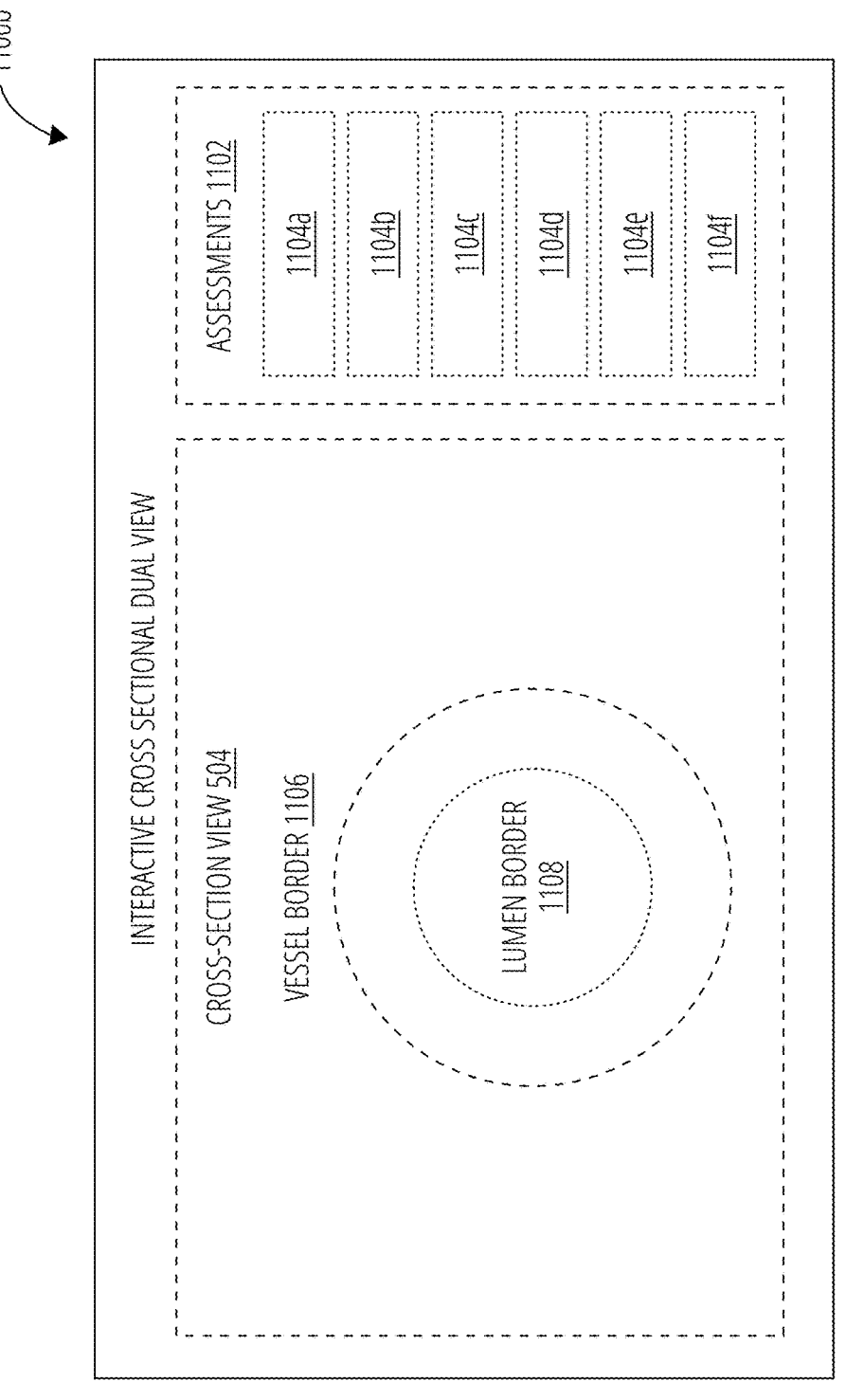
FIG. 11B illustrates a fourth graphical component of a graphical interface for an IVUS imaging system.

FIG. 11A and FIG. 11B illustrate interactive cross sectional dual views 1100a and 1100b, respectively, according to some embodiments of the present disclosure. IVUS images visualization system 400 can be configured to generate interactive cross sectional dual views 1100a or 1100b as interactive cross-section view 902. As depicted, interactive cross sectional dual views 1100a and 1100b include a GUI component depicting or representing cross-section view 504 (e.g., corresponding to the point in IVUS images 418 at which view slider 708 is disposed) as well as depictions of representations of assessments 424, represented as assessments 1102 GUI components. In general, assessments 1102 can comprise several indications (e.g., icons, graphics, cartoons, text, or the like) such as indications 1104a, 1104b, 1104c, 1104d, 1104e, and 1104f.

As described above, in some embodiments, indications of vessel and lumen borders can be depicted. FIG. 11B and interactive cross sectional dual view 1100b comprise the GUI components of interactive cross sectional dual view 1100a in addition to vessel border 1106 and lumen border 1108. With some examples, processor 406 can execute instructions 416 to generate interactive cross sectional dual view 1100b as interactive cross-section view 902 responsive to activation of vessel navigation 506 where the vessel border 1106 and lumen border 1108 are defaulted to "visible" and generate interactive cross sectional dual view 1100a responsive to activation of viewing buttons 614 indicating that borders are to be disabled to give a clear view of the cross-section representation of the vessel depicted in interactive cross-section view 902.

Figure 12A:
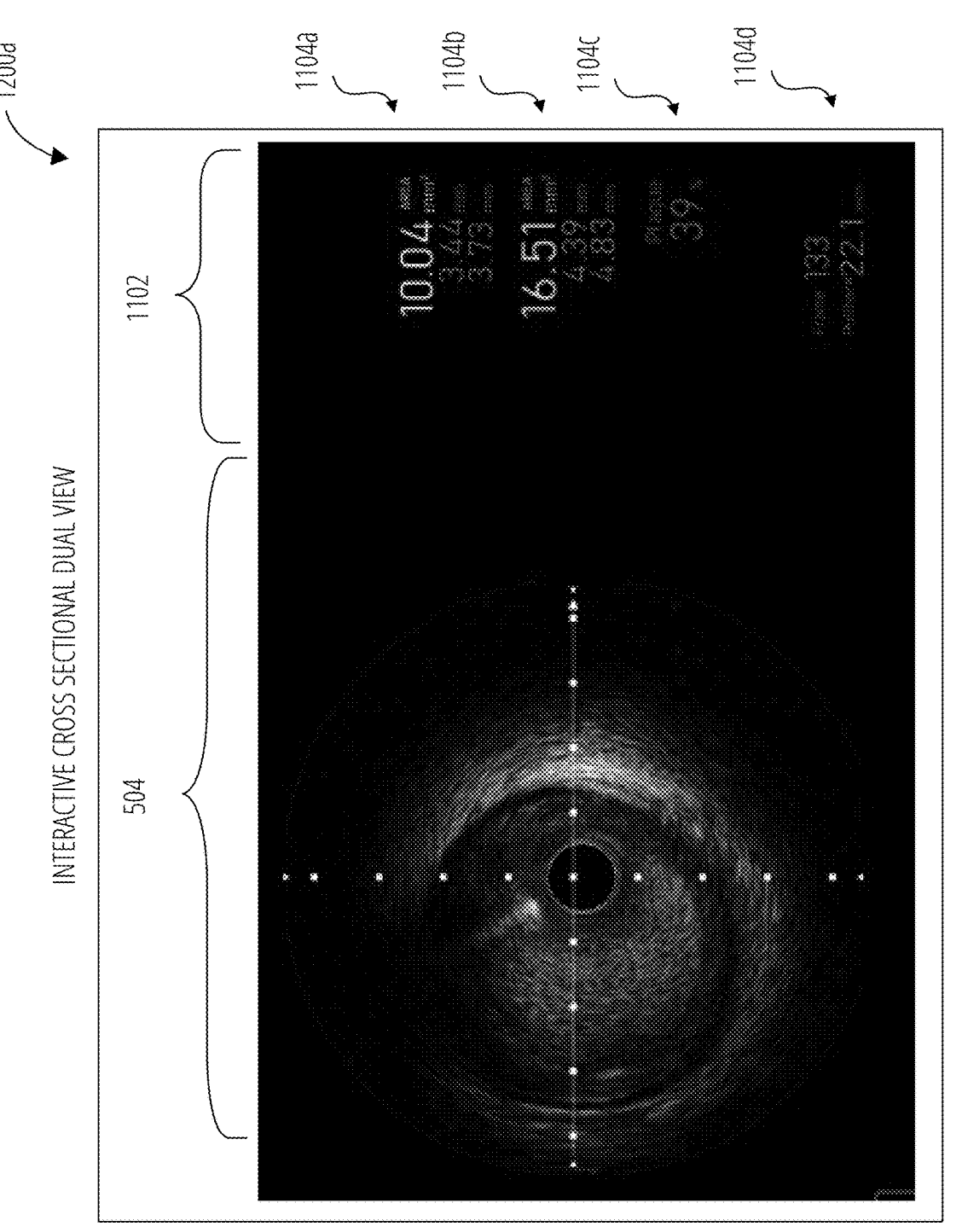
FIGS. 12A, 12B, and 12C illustrate versions of a fifth graphical component of a graphical interface for an IVUS imaging system.

FIG. 12A illustrates an interactive cross sectional dual view 1200a, which can be generated according to some embodiments of the present disclosure. For example, interactive cross sectional dual view 1200a can be generated by IVUS images visualization system 400 as interactive cross-section view 902 of GUI 422 and displayed on display 404. With some embodiments, as depicted, interactive cross sectional dual view 1200a includes cross-section view 504 and assessments 1102. Assessments 1102 includes indications 1104a, 1104b, 1104c, and 1104d, which depict, respectively, the lumen area and cross-section diameters, the vessel area and cross-section diameters, the plaque burden (e.g., ration of lumen to vessel area) and the frame number (e.g., image number in the series of IVUS images 418) as well as the distance from the distal starting point of the IVUS images 418.

Figure 12B:
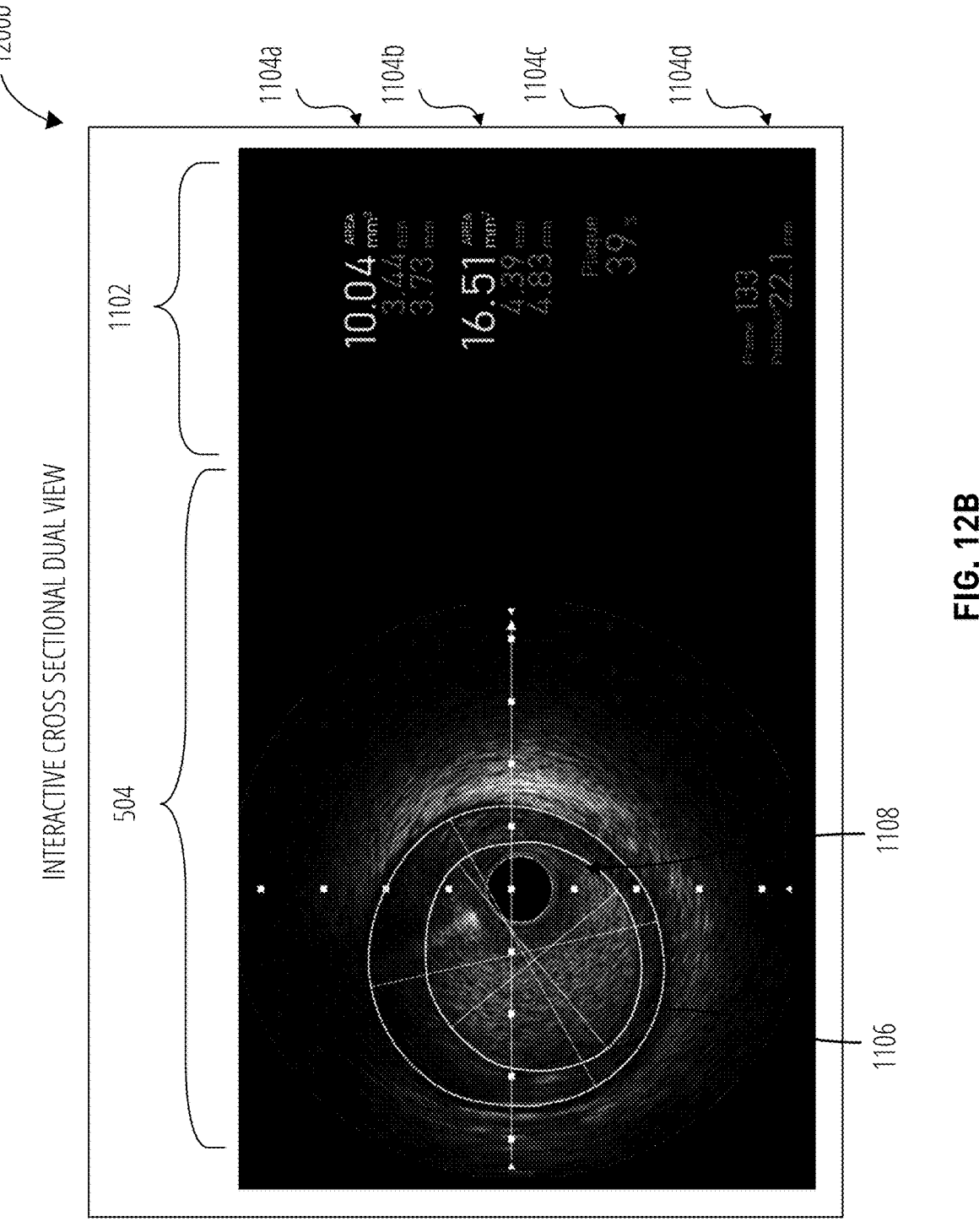

FIG. 12B illustrates an interactive cross sectional dual view 1200b, which can be generated according to some embodiments of the present disclosure. For example, interactive cross sectional dual view 1200b can be generated by IVUS images visualization system 400 as interactive cross-section view 902 of GUI 422 and displayed on display 404. With some embodiments, as depicted, interactive cross sectional dual view 1200b includes cross-section view 504 and assessments 1102.

The cross-section view 504 includes depictions of the vessel border 1106 and lumen border 1108 as well as cross-sectional diameters of the vessel and lumen. Assessments 1102 includes indications 1104a, 1104b, 1104c, and 1104d, which depict, respectively, the lumen area and cross-section diameters, the vessel area and cross-section diameters, the plaque burden (e.g., ration of lumen to vessel area) and the frame number (e.g., image number in the series of IVUS images 418) as well as the distance from the distal starting point of the IVUS images 418.

Figure 12C:
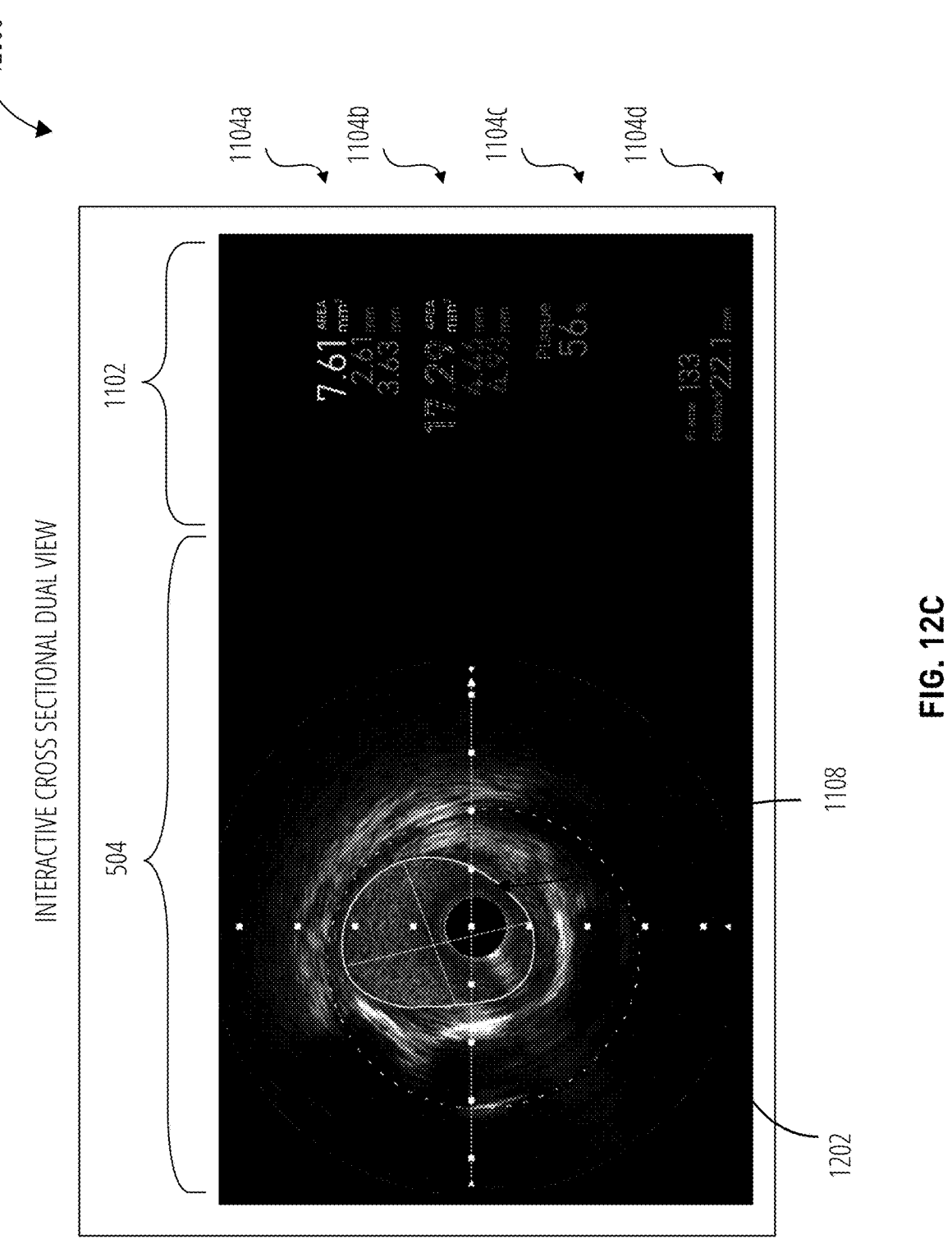

FIG. 12C illustrates an interactive cross sectional dual view 1200c, which can be generated according to some embodiments of the present disclosure. For example, interactive cross sectional dual view 1200c can be generated by IVUS images visualization system 400 as interactive cross-section view 902 of GUI 422 and displayed on display 404. With some embodiments, as depicted, interactive cross sectional dual view 1200c includes cross-section view 504 and assessments 1102.

The cross-section view 504 includes depictions of the vessel border 1106 and lumen border 1108 as well as cross-sectional diameters of the vessel and lumen. Assessments 1102 includes indications 1104a, 1104b, 1104c, and 1104d, which depict, respectively, the lumen area and cross-section diameters, the vessel area and cross-section diameters, the plaque burden (e.g., ration of lumen to vessel area) and the frame number (e.g., image number in the series of IVUS images 418) as well as the distance from the distal starting point of the IVUS images 418.

With some embodiments, automatic border detection may be of low confidence. For example, where machine learning is used to automatically detect the vessel and lumen borders, the detection may include a confidence score. In such examples, where the confidence score is below a threshold, the depictions of the border can change to convey the low confidence in the border. For example, the cross-section view of the vessel depicted in FIG. 12C is attenuated, and the vessel border has a low confidence. As such, the lumen border 1108 is shown as a broken or dashed line as opposed to a solid line.

In many examples, the borders (e.g., vessel border 1106, lumen border 1108, lumen border 1108, or the like) are editable. For example, a user can manipulate or change the borders (e.g., via I/O devices 410, or the like). In some embodiments, processor 406 can execute instructions 416 to change lumen border 1108 to a regular border (e.g., vessel border 1106, 1108, or the like) responsive to manipulation or modification by a user. Processor 406 can execute instructions 416 to receive indications of a modification to lumen border 1108 and can change lumen border 1108 to vessel border 1106 or lumen border 1108 (as may be the case) based on the modification.

Further, in some embodiments, the depiction of the assessments 1102 can change based on the confidence of the assessment. For example, the vessel area depicted in 1104b is shown in broken or with a dashed outline. Processor 406 can execute instructions 416 to change the depiction or representation of portions of assessments 1102 based on modification from a user. For example, where a user modifies a lumen border 1108, the border and the corresponding indication (e.g., 1104*b*) can be changed to indicate the higher confidence based on user modification.

Figure 13:
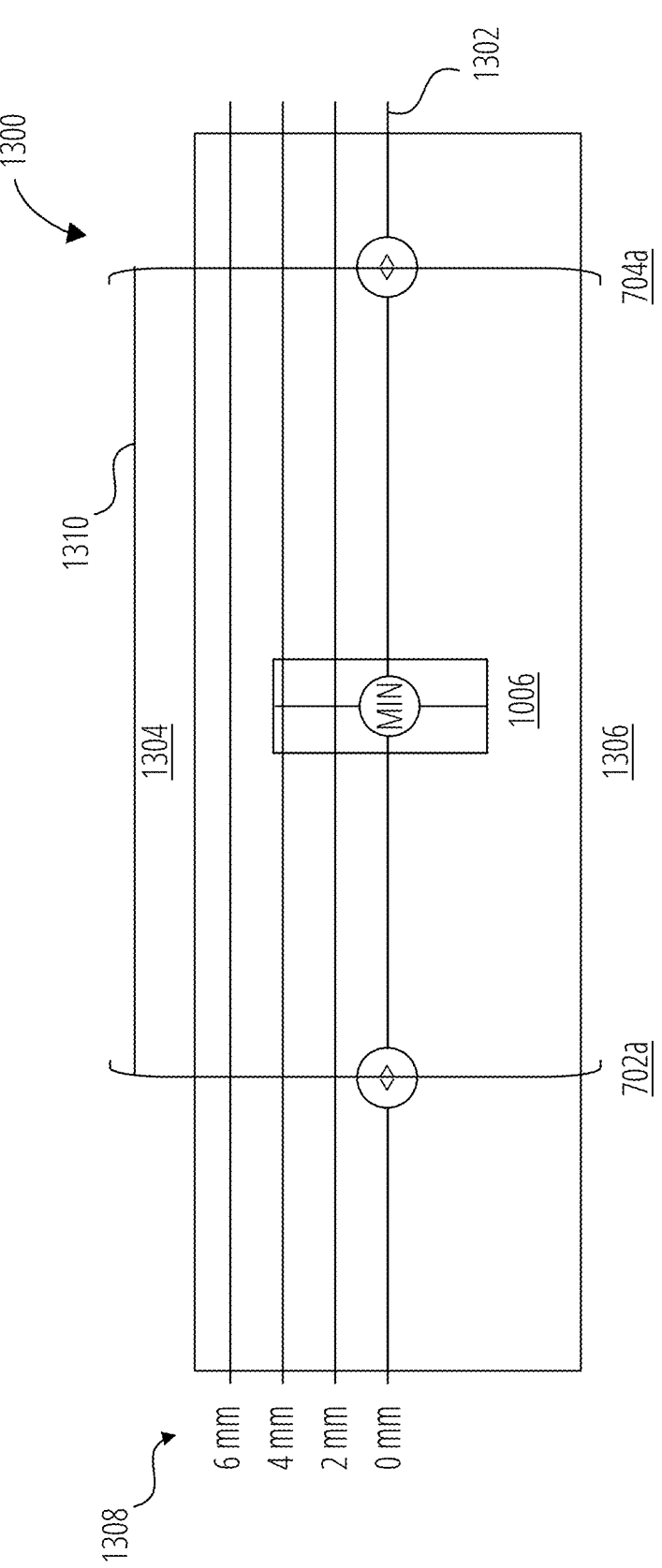
FIG. 13 illustrates a sixth graphical component of a graphical interface for an IVUS imaging system.

FIG. 13 illustrates profile view 1300, according to some embodiments of the present disclosure. IVUS images visualization system 400 can be configured to generate profile view 1300 as interactive vessel navigation 904. As depicted, profile view 1300 includes several GUI components including a central axis 1302 about which longitudinal border profile 1304 and longitudinal border profile mirror reflection 1306 are disposed. Examples of longitudinal border profile 1304 and 1306 are given below. However, in general, 1304 depicts or is representative of the detected borders (e.g., vessel border 1106, lumen border 1108, lumen border 1108, etc.) for the IVUS images 418. Longitudinal border profile mirror reflection 1306 is a mirror reflection of the longitudinal border profile 1304, thereby providing a more complete visualization of the vessel and lumen profile.

Profile view 1300 further includes scale 1308 depicting the radius of the detected borders represented in longitudinal border profile 1304. Additionally, profile view 1300 includes proximal bracket end 702*a* and distal bracket end 704*a* (or proximal bracket end 702*b* and distal bracket end 704*b* as may be the case) as well as minimum region 1006. Each of the brackets are movable via user input (e.g., via I/O devices 410). Furthermore, with some examples, ruler 1310 can be enabled (e.g., by default, by input button selection, or the like) and can measure a distance between brackets (e.g., proximal bracket end 702*a* and distal bracket end 704*a*, or the like).

Figures 14A, 14B:
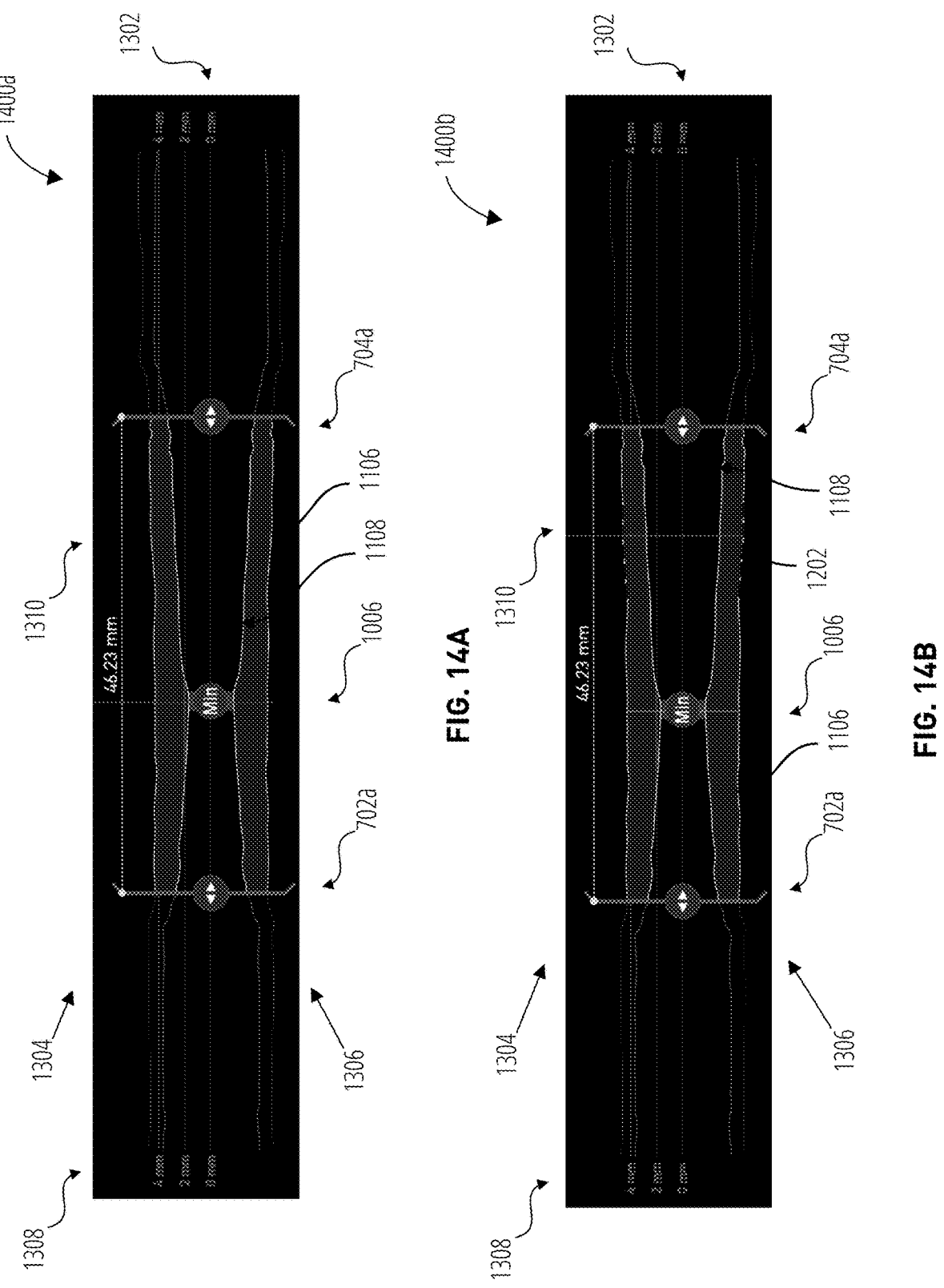
FIGS. 14A and 14B illustrate versions of a seventh graphical component of a graphical interface for an IVUS imaging system.

FIG. 14A illustrates a profile view 1400*a*, which can be generated according to some embodiments of the present disclosure. For example, profile view 1400*a* can be generated by IVUS images visualization system 400 as interactive vessel navigation 904 of GUI 422 and displayed on display 404. As depicted, profile view 1400*a* can include longitudinal border profile 1304 and longitudinal border profile mirror reflection 1306 which each include vessel border 1106 and lumen border 1108. Note, in some embodiments, processor 406 can execute instructions 416 to shade or color the area between vessel border 1106 and lumen border 1108 to indicate plaque. Additionally, profile view 1400*a* can include proximal bracket end 702*a*, distal bracket end 704*a*, and minimum region 1006. Further, although not shown, profile view 1400*a* can include central axis 1302 and scale 1308.

FIG. 14B illustrates a 1400*a*, which can be generated according to some embodiments of the present disclosure. As noted above, with some examples, the detected borders can have a low confidence. In such an example, the borders represented in the profile view can be generated to indicate the low confidence of the borders. For example, profile view 1400*b* includes GUI components of profile view 1400*a* with the difference that lumen border 1108, or rather the portions of the vessel border 1106 that is low confidence is indicated by broken lines for the border. For example, frames of IVUS images 418 that have low confidence borders, such as a section of frames, can be depicted (or denoted) by a different line profile than the sections of IVUS images 418 that are above a confidence threshold.

Figure 15:
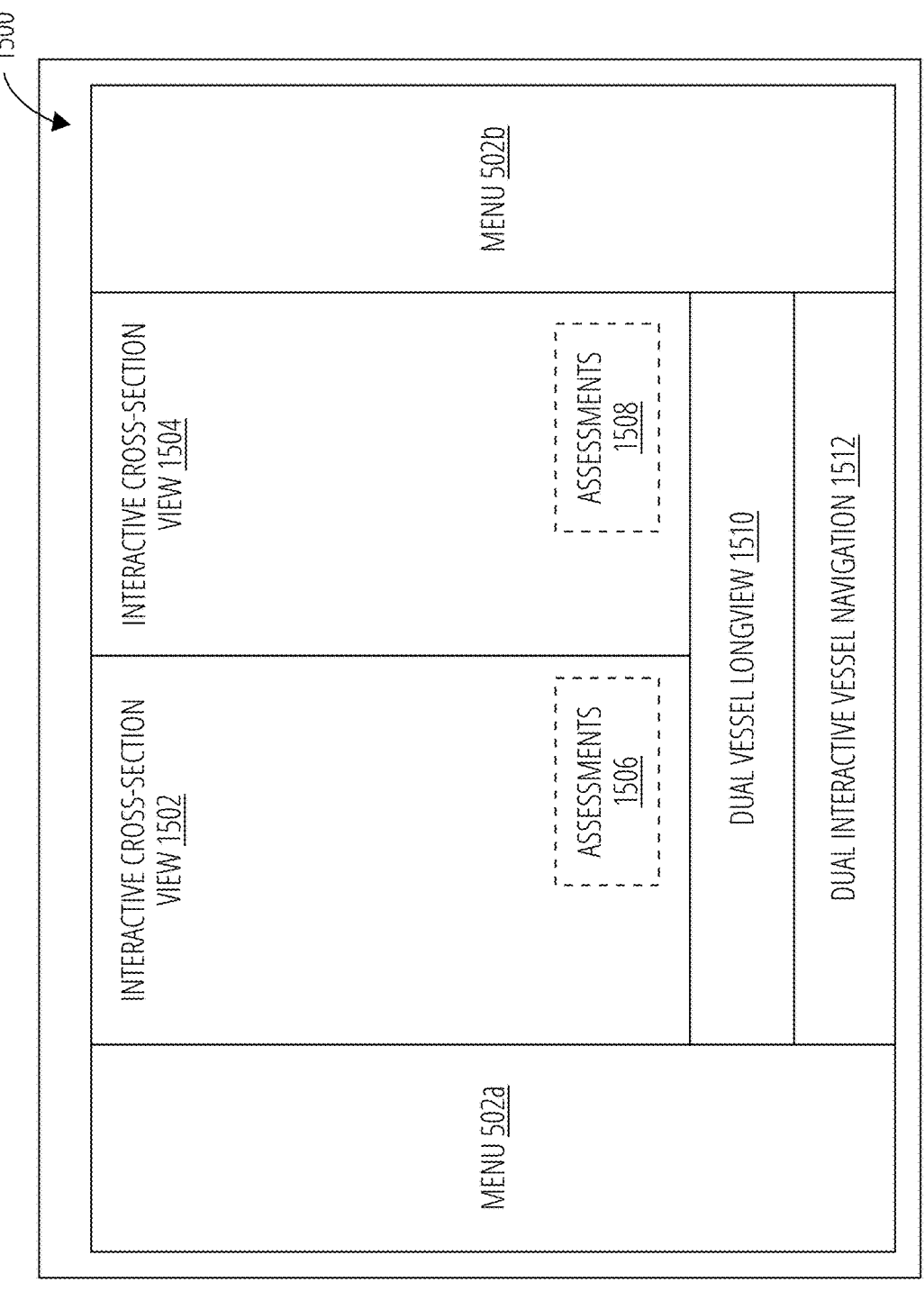
FIG. 15 illustrates a ninth graphical interface for an IVUS imaging system.

FIG. 15 illustrates a GUI 1500, which can be generated according to some embodiments of the present disclosure. For example, GUI 1500 can be generated by IVUS images visualization system 400 as GUI 422 and displayed on display 404. As depicted, GUI 1500 includes several graphical information elements 420 like previous GUIs (e.g., GUI 900*a*, GUI 900*b*, etc.) However, GUI 1500 comprises a dual-view or side-by-side view of cross-section areas. In some embodiments, the side-by-side view can be enabled via buttons in one of menus 502*a* or 502*b* (e.g., via layout buttons 612, or the like).

As depicted, GUI 1500 includes interactive cross-section view 1502 and interactive cross-section view 1504 disposed side-by-side between menu 502*a* and menu 502*b*. Interactive cross-section interactive cross-section views 1502 and 1504 can each include assessments 1506 and 1508, respectively, which list assessments for the respective frame depicted in views interactive cross-section views 1502 and 1504.

GUI 1500 further includes dual vessel long view 1510 and 1512. In general, dual vessel long view 1510 and dual interactive vessel navigation 1512 can be like prior vessel long views (e.g., vessel navigation 506, or the like) and vessel navigation GUI components (e.g., interactive vessel navigation 904, or the like) with the exception that dual view GUI components include two sliders (e.g., view slider 708).

Figure 16:
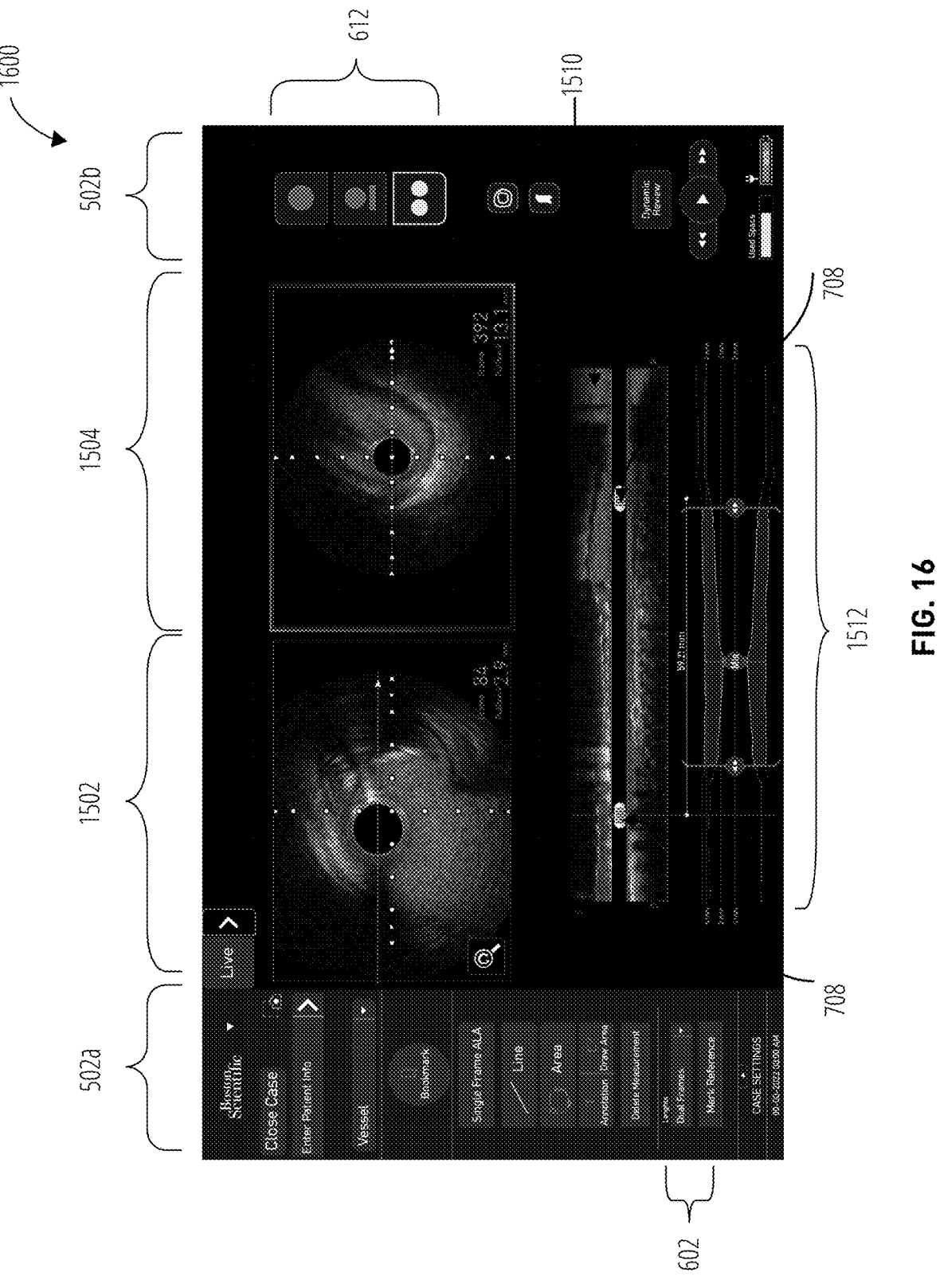
FIG. 16 illustrates a tenth graphical interface for an IVUS imaging system.

FIG. 16 illustrates a GUI 1600, which can be generated according to some embodiments of the present disclosure. For example, GUI 1600 can be generated by IVUS images visualization system 400 as GUI 422 and displayed on display 404. With some embodiments, responsive to activation of the dual layout (e.g., via layout buttons 612, or the like) processor 406 can execute instructions 416 to generate graphical information elements 420 and GUI 1600 from graphical information elements 420.

As depicted, GUI 1600 includes a first cross-section interactive cross-section view 1502 disposed side-by-side next to a second interactive cross-section view 1504, both framed by menu 502*a* and menu 502*b*. Further, GUI 1600 includes dual vessel long view 1510 and dual interactive vessel navigation 1512 disposed below the interactive cross-section view 1502 and interactive cross-section view 1504. Dual vessel long view 1510 includes a view slider 708 for each cross-section view. For example, a first slider 708 and a second slider 708 are depicted. With some embodiments, the sliders and cross-section views can be color coordinated to indicate which slider controls which view. Further, in some embodiments, ruler 1310 can be enabled (e.g., via length measurements inputs 602, or the like). As depicted, ruler 1310 shows the distance between the respective frames depicted the interactive cross-section view 1502 and interactive cross-section view 1504.

FIG. 17 illustrates a logic flow 1700 to generate a GUI, according to some embodiments of the present disclosure. The logic flow 1700 can be implemented by IVUS images visualization system 400 and will be described with reference to IVUS images visualization system 400 for clarity of presentation. However, it is noted that logic flow 1700 could also be implemented by an IVUS guidance system different than IVUS images visualization system 400.

Logic flow 1700 can begin at block 1702. At block 1702 "receive a series of intravascular ultrasound (IVUS) images of a vessel of a patient, the series of IVUS images comprising a plurality of frames" a series of IVUS images captured via an IVUS catheter percutaneously inserted in a vessel of a patent can be received. For example, information elements comprising indications of IVUS images 418 can be received from IVUS imaging system 100 where catheter 102 is (or was) percutaneously inserted into vessel 202. The IVUS images 418 can comprise frames of images representative of images captured while the catheter 102 is pulled back from distal end 204 to proximal end 206. Processor 406 can execute instructions 416 to receive information elements comprising indications of IVUS images 418 from IVUS imaging system 100, or directly from catheter 102 as may be the case.

Continuing to block 1704 "generate a first graphical user interface (GUI) component comprising an indication of a cross-section view of a one of the plurality of frames" a first GUI component comprising an indication of a cross-section view of a one of the plurality of frames is generated. For example, processor 406 can execute instructions 416 to generate a cross-section view (e.g., cross-section view 504, interactive cross-section view 902, or the like).

Continuing to block 1706 "generate a second GUI component comprising indications of at least one menu option" a second GUI component comprising indications of at least one menu option is generated. For example, processor 406 can execute instructions 416 to generate menu 502a. Continuing to block 1708 "generate a third GUI component comprising indications of at least one layout option" a third GUI component comprising indications of at least one layout option is generated. For example, processor 406 can execute instructions 416 to generate menu 502b. Continuing to block 1708 "generate a fourth GUI component comprising indications of navigation inputs" a fourth GUI component comprising indications of navigation inputs is generated. For processor 406 can execute instructions 416 to generate vessel navigation 506.

Continuing to block 1712 "generate a GUI comprising the first, second, third, and fourth GUI components, wherein the first GUI component is disposed between the second and third GUI components" a GUI comprising the first, second, third, and fourth GUI components where the first GUI component is disposed between the second and third GUI components is generated. For example, processor 406 can execute instructions 416 to generate GUI 422. Continuing to block 1714 "render the GUI for display on a display" the GUI can be rendered for display. For example, processor 406 can execute instructions 416 to render the GUI components and GUI for display on display 404.

Figure 18:
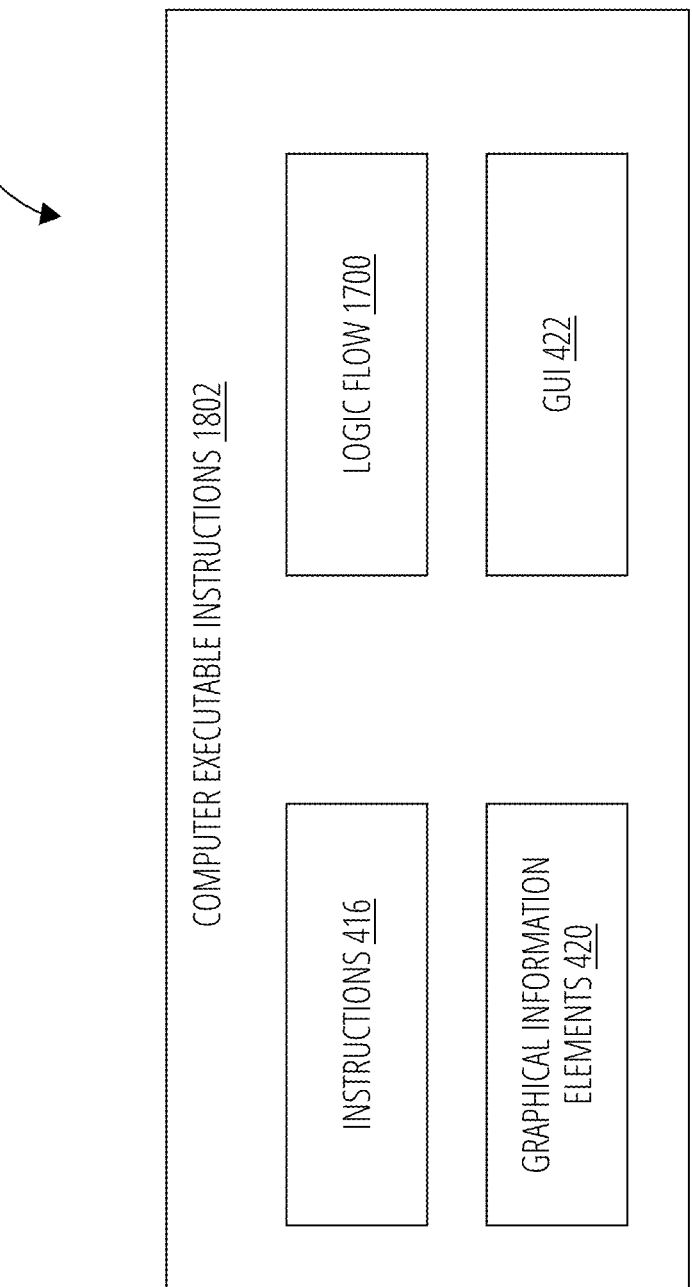
FIG. 18 illustrates a computer-readable storage medium.

FIG. 18 illustrates computer-readable storage medium 1800. Computer-readable storage medium 1800 may comprise any non-transitory computer-readable storage medium or machine-readable storage medium, such as an optical, magnetic or semiconductor storage medium. In various embodiments, computer-readable storage medium 1800 may comprise an article of manufacture. In some embodiments, computer-readable storage medium 1800 may store computer executable instructions 1802 with which circuitry (e.g., processor 106, processor 406, IVUS imaging system acquisition circuitry 414, and the like) can execute. For example, computer executable instructions 1802 can include instructions to implement operations described with respect to instructions 416, logic flow 1700, graphical information elements 420, and/or GUI 422. Examples of computer-readable storage medium 1800 or machine-readable storage medium may include any tangible media capable of storing electronic data, including volatile memory or non-volatile memory, removable or non-removable memory, erasable or non-erasable memory, writeable or re-writeable memory, and so forth. Examples of computer executable instructions 1802 may include any suitable type of code, such as source code, compiled code, interpreted code, executable code, static code, dynamic code, object-oriented code, visual code, and the like.

Figure 19:
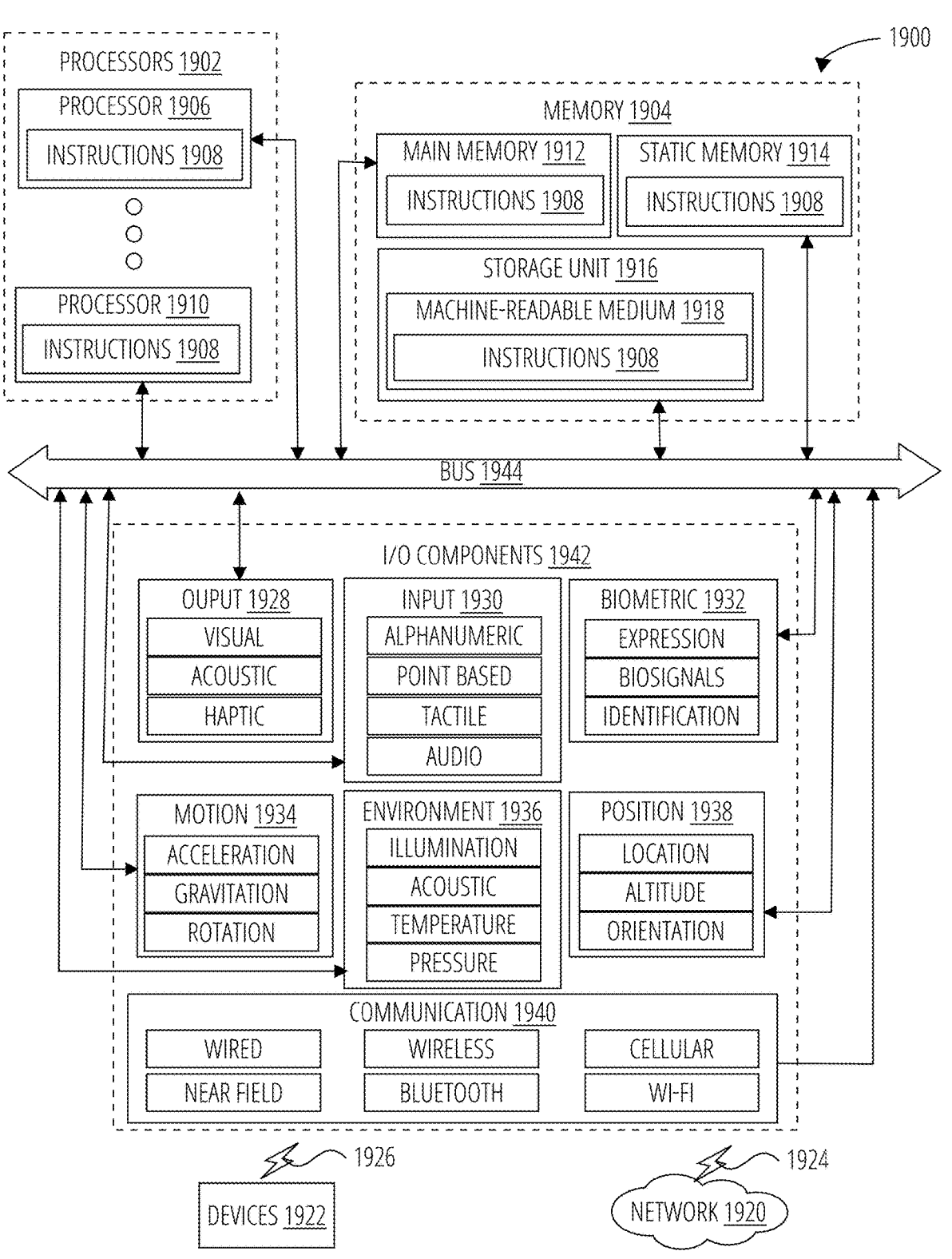
FIG. 19 illustrates a diagrammatic representation of a machine.

FIG. 19 illustrates a diagrammatic representation of a machine 1900 in the form of a computer system within which a set of instructions may be executed for causing the machine to perform any one or more of the methodologies discussed herein. More specifically, FIG. 19 shows a diagrammatic representation of the machine 1900 in the example form of a computer system, within which instructions 1908 (e.g., software, a program, an application, an applet, an app, or other executable code) for causing the machine 1900 to perform any one or more of the methodologies discussed herein may be executed. For example, the instructions 1908 may cause the machine 1900 to execute logic flow 1700 of FIG. 17, instructions 416 of FIG. 4. More generally, the instructions 1908 may cause the machine 1900 to generate GUIs with functionality and behavior as described herein during a pre-PCI, peri-PCI, or post-PCI using IVUS. It is noted that the present disclosure provides specific and discrete implementations of GUI representations and behavior that is a significant improvement over the prior art. In particular, the present disclosure provides an improvement to computing technology in that GUIs provide greater visibility and navigation of IVUS images.

The instructions 1908 transform the general, non-programmed machine 1900 into a particular machine 1900 programmed to carry out the described and illustrated functions in a specific manner. In alternative embodiments, the machine 1900 operates as a standalone device or may be coupled (e.g., networked) to other machines. In a networked deployment, the machine 1900 may operate in the capacity of a server machine or a client machine in a server-client network environment, or as a peer machine in a peer-to-peer (or distributed) network environment. The machine 1900 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1908, sequentially or otherwise, that specify actions to be taken by the machine 1900. Further, while only a single machine 1900 is illustrated, the term "machine" shall also be taken to include a collection of machines 1900 that individually or jointly execute the instructions 1908 to perform any one or more of the methodologies discussed herein.

The machine 1900 may include processors 1902, memory 1904, and I/O components 1942, which may be configured to communicate with each other such as via a bus 1944. In an example embodiment, the processors 1902 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an ASIC, a Radio-Frequency Integrated Circuit (RFIC), another processor, or any suitable combination thereof) may include, for example, a processor 1906 and a processor 1910 that may execute the instructions 1908. The term "processor" is intended to include multi-core processors that may comprise two or more independent processors (sometimes referred to as "cores") that may execute instructions contemporaneously. Although FIG. 19 shows multiple processors 1902, the machine 1900 may include a single processor with a single core, a single processor with multiple cores (e.g., a multi-core processor), multiple processors with a single core, multiple processors with multiples cores, or any combination thereof.

The memory 1904 may include a main memory 1912, a static memory 1914, and a storage unit 1916, both accessible to the processors 1902 such as via the bus 1944. The main memory 1904, the static memory 1914, and storage unit 1916 store the instructions 1908 embodying any one or more of the methodologies or functions described herein. The instructions 1908 may also reside, completely or partially, within the main memory 1912, within the static memory 1914, within machine-readable medium 1918 within the storage unit 1916, within at least one of the processors 1902 (e.g., within the processor's cache memory), or any suitable combination thereof, during execution thereof by the machine 1900.

The I/O components 1942 may include a wide variety of components to receive input, provide output, produce output, transmit information, exchange information, capture measurements, and so on. The specific I/O components 1942 that are included in a particular machine will depend on the type of machine. For example, portable machines such as mobile phones will likely include a touch input device or other such input mechanisms, while a headless server machine will likely not include such a touch input device. It will be appreciated that the I/O components 1942 may include many other components that are not shown in FIG. 19. The I/O components 1942 are grouped according to functionality merely for simplifying the following discussion and the grouping is in no way limiting. In various example embodiments, the I/O components 1942 may include output components 1928 and input components 1930. The output components 1928 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1930 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 1942 may include biometric components 1932, motion components 1934, environmental components 1936, or position components 1938, among a wide array of other components. For example, the biometric components 1932 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1934 may include acceleration sensor components (e.g., accelerometer), gravitation sensor components, rotation sensor components (e.g., gyroscope), and so forth. The environmental components 1936 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1938 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1942 may include communication components 1940 operable to couple the machine 1900 to a network 1920 or devices 1922 via a coupling 1924 and a coupling 1926, respectively. For example, the communication components 1940 may include a network interface component or another suitable device to interface with the network 1920. In further examples, the communication components 1940 may include wired communication components, wireless communication components, cellular communication components, Near Field Communication (NFC) components, Bluetooth® components (e.g., Bluetooth® Low Energy), Wi-Fi© components, and other communication components to provide communication via other modalities. The devices 1922 may be another machine or any of a wide variety of peripheral devices (e.g., a peripheral device coupled via a USB).

Moreover, the communication components 1940 may detect identifiers or include components operable to detect identifiers. For example, the communication components 1940 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1940, such as location via Internet Protocol (IP) geolocation, location via Wi-Fi® signal triangulation, location via detecting an NFC beacon signal that may indicate a particular location, and so forth.

The various memories (i.e., memory 1904, main memory 1912, static memory 1914, and/or memory of the processors 1902) and/or storage unit 1916 may store one or more sets of instructions and data structures (e.g., software) embodying or utilized by any one or more of the methodologies or functions described herein. These instructions (e.g., the instructions 1908), when executed by processors 1902, cause various operations to implement the disclosed embodiments.

As used herein, the terms "machine-storage medium," "device-storage medium," "computer-storage medium" mean the same thing and may be used interchangeably in this disclosure. The terms refer to a single or multiple storage devices and/or media (e.g., a centralized or distributed database, and/or associated caches and servers) that store executable instructions and/or data. The terms shall accordingly be taken to include, but not be limited to, solid-state memories, and optical and magnetic media, including memory internal or external to processors. Specific examples of machine-storage media, computer-storage media and/or device-storage media include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms "machine-storage media," "computer-storage media," and "device-storage media" specifically exclude carrier waves, modulated data signals, and other such media, at least some of which are covered under the term "signal medium" discussed below.

In various example embodiments, one or more portions of the network 1920 may be an ad hoc network, an intranet, an extranet, a VPN, a LAN, a WLAN, a WAN, a WWAN, a MAN, the Internet, a portion of the Internet, a portion of the PSTN, a plain old telephone service (POTS) network, a cellular telephone network, a wireless network, a Wi-Fi® network, another type of network, or a combination of two or more such networks. For example, the network 1920 or a portion of the network 1920 may include a wireless or cellular network, and the coupling 1924 may be a Code Division Multiple Access (CDMA) connection, a Global System for Mobile communications (GSM) connection, or another type of cellular or wireless coupling. In this example, the coupling 1924 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard-setting organizations, other long range protocols, or other data transfer technology.

The instructions 1908 may be transmitted or received over the network 1920 using a transmission medium via a network interface device (e.g., a network interface component included in the communication components 1940) and utilizing any one of several well-known transfer protocols (e.g., hypertext transfer protocol (HTTP)). Similarly, the instructions 1908 may be transmitted or received using a transmission medium via the coupling 1926 (e.g., a peer-to-peer coupling) to the devices 1922. The terms "transmission medium" and "signal medium" mean the same thing and may be used interchangeably in this disclosure. The terms "transmission medium" and "signal medium" shall be taken to include any intangible medium that can store, encoding, or carrying the instructions 1908 for execution by the machine 1900, and includes digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a matter as to encode information in the signal.

Terms used herein should be accorded their ordinary meaning in the relevant arts, or the meaning indicated by their use in context, but if an express definition is provided, that meaning controls.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to one or multiple ones. Additionally, the words "herein," "above," "below" and words of similar import, when used in this application, refer to this application as a whole and not to any portions of this application. When the claims use the word "or" in reference to a list of two or more items, that word covers all the following interpretations of the word: any of the items in the list, all the items in the list and any combination of the items in the list, unless expressly limited to one or the other. Any terms not expressly defined herein have their conventional meaning as commonly understood by those having skill in the relevant art(s).

By using genuine models of anatomy more accurate surgical plans may be developed than through statistical modeling.

Terms used herein should be accorded their ordinary meaning in the relevant arts, or the meaning indicated by their use in context, but if an express definition is provided, that meaning controls.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to one or multiple ones. Additionally, the words "herein," "above," "below" and words of similar import, when used in this application, refer to this application as a whole and not to any portions of this application. When the claims use the word "or" in reference to a list of two or more items, that word covers all the following interpretations of the word: any of the items in the list, all the items in the list and any combination of the items in the list, unless expressly limited to one or the other. Any terms not expressly defined herein have their conventional meaning as commonly understood by those having skill in the relevant art(s).

What is claimed is:

1. An apparatus for an intravascular ultrasound (IVUS) imaging system, comprising:
a display;
an interface configured to couple to an IVUS catheter;
a processor coupled to the interface and the display; and
a memory device comprising instructions, which when executed by the processor cause the IVUS imaging system to:
receive a series of intravascular ultrasound (IVUS) images of a vessel of a patient, the series of IVUS images comprising a plurality of frames;
generate a first graphical user interface (GUI) component comprising an indication of a cross-section view of a one of the plurality of frames;
generate a second GUI component comprising indications of at least one menu option;

generate a third GUI component comprising indications of at least one layout option;

generate a fourth GUI component comprising indications of navigation inputs, the navigation inputs comprising an assessment button and a distal bracket and a proximal bracket, wherein the distal bracket and the proximal bracket are moveable;

determine a distance between the distal bracket and the proximal bracket;

generate the indication of the assessment button based on the distance;

generate a GUI comprising the first, second, third, and fourth GUI components, wherein the first GUI component is disposed between the second and third GUI components; and render the GUI and send the rendered GUI graphical information to the display.

2. The apparatus of claim 1, the memory device further comprising instructions that when executed by the processor cause the IVUS imaging system to receive, via an input device, an indication to move the distal bracket, the proximal bracket, or the distal bracket and the proximal bracket.

3. The apparatus of claim 2, the memory device further comprising instructions that when executed by the processor cause the IVUS imaging system to regenerate the fourth GUI component comprising graphical indications of the moved distal bracket, the moved proximal bracket, or the moved distal and proximal bracket and the assessment button.

4. The apparatus of claim 1, wherein the assessment button is disposed between the proximal bracket and the distal bracket.

5. The apparatus of claim 1, the memory device further comprising instructions that when executed by the processor cause the IVUS imaging system to:

determine whether the distance is greater than a threshold; and generate the indication of the assessment button comprising a graphical representation including at least an icon and text based on a determination that the distance is greater than the threshold.

6. The apparatus of claim 5, the memory device further comprising instructions that when executed by the processor cause the IVUS imaging system to generate the indication of the assessment button comprising a graphical representation including one but not both of text or an icon based on a determination that the distance is less than or equal to the threshold.

7. At least one machine readable storage device, comprising a plurality of instructions that in response to being executed by a processor of an intravascular ultrasound (IVUS) imaging system cause the processor to:

receive a series of intravascular ultrasound (IVUS) images of a vessel of a patient, the series of IVUS images comprising a plurality of frames;

generate a first graphical user interface (GUI) component comprising an indication of a cross-section view of a one of the plurality of frames;

generate a second GUI component comprising indications of at least one menu option;

generate a third GUI component comprising indications of at least one layout option;

generate a fourth GUI component comprising indications of navigation inputs, the navigation inputs comprising an assessment button and a distal bracket and a proximal bracket, wherein the distal bracket and the proximal bracket are moveable;

determine a distance between the distal bracket and the proximal bracket;

generate the indication of the assessment button based on the distance;

generate a GUI comprising the first, second, third, and fourth GUI components, wherein the first GUI component is disposed between the second and third GUI components; and render the GUI for display on a display.

8. The at least one machine readable storage device of claim 7, further comprising instructions that in response to being executed by the processor cause the processor to:

receive an indication, via an input device, the assessment button was clicked; and generate a fifth GUI component comprising an indication of a distal bracket, a proximal bracket, a minimum region, a vessel profile view and a mirror of the vessel profile view.

9. The at least one machine readable storage device of claim 8, wherein the vessel profile view comprises an indication of a border of the vessel and a border of a lumen within the vessel represented along a longitudinal axis of the vessel.

10. The at least one machine readable storage device of claim 9, further comprising instructions that in response to being executed by the processor cause the processor to:

receive an indication of the border of the vessel border and the border of the lumen border for each of the plurality of frames;

generate a graphical representation of the border of the vessel and the border of the lumen based on the indication;

generate the vessel profile view comprising the graphical representation of the border of the vessel and the border of the lumen; and mirror the vessel profile view about a central longitudinal axis to generate the mirror of the vessel profile view.

11. The at least one machine readable storage device of claim 10, further comprising instructions that in response to being executed by the processor cause the processor to:

receive, from a machine learning automated border detection model, the indication of the border of the vessel border and the border of the lumen border;

receive an indication of a confidence of the border of the vessel border for each of the plurality of frames;

determine, for each of the plurality of frames, whether the confidence is less than or equal to a threshold confidence level; and generate the graphical representation of the border of the vessel border for a first portion of the central longitudinal axis comprising a first graphical representation based on a determination that the confidence is less than or equal to the threshold for the plurality of frames associated with the first portion; and generate the graphical representation of the border of the vessel border for a second portion of the central longitudinal axis comprising a second graphical representation based on a determination that the confidence is not less than or equal to the threshold for the plurality of frames associated with the second portion, wherein the second graphical representation is different than the first graphical representation.

12. The at least one machine readable storage device of claim 11, wherein the first graphical representation comprises a first color, first width, or first style of line and wherein the second graphical representation comprises a second color, second width, or second style of line.

13. A method for an intravascular ultrasound (IVUS) imaging system, comprising:

receiving a series of intravascular ultrasound (IVUS) images of a vessel of a patient, the series of IVUS images comprising a plurality of frames;

generating a first graphical user interface (GUI) component comprising an indication of a cross-section view of a one of the plurality of frames;

generating a second GUI component comprising indications of at least one menu option;

generating a third GUI component comprising indications of at least one layout option;

generating a fourth GUI component comprising indications of navigation inputs, the navigation inputs comprising an assessment button and a distal bracket and a proximal bracket, wherein the distal bracket and the proximal bracket are moveable;

determine a distance between the distal bracket and the proximal bracket;

generate the indication of the assessment button based on the distance;

generating a GUI comprising the first, second, third, and fourth GUI components, wherein the first GUI component is disposed between the second and third GUI components; and rendering the GUI for display on a display.

14. The method of claim 13, generating the fourth GUI component comprising indications of the assessment button and a distal bracket and a proximal bracket, wherein the distal bracket and the proximal bracket are moveable.

15. The method of claim 14, comprising receiving an indication, via an input device, to move the distal bracket, the proximal bracket, or the distal bracket and the proximal bracket.

16. The method of claim 15, comprising regenerating the fourth GUI component comprising graphical indications of the moved distal bracket, the moved proximal bracket, or the moved distal and proximal bracket and the assessment button.

17. The method of claim 14, wherein the assessment button is disposed between the proximal bracket and the distal bracket.

18. The method of claim 17, comprising:

determining a distance between the distal bracket and the proximal bracket; and generating the indication of the assessment button based on the distance.

* * * * *